(12) United States Patent
Quake et al.

(10) Patent No.: US 9,777,329 B2
(45) Date of Patent: *Oct. 3, 2017

(54) NON-INVASIVE FETAL GENETIC SCREENING BY DIGITAL ANALYSIS

(75) Inventors: Stephen Quake, Stanford, CA (US); Hei-Mun Christina Fan, Fremont, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1221 days.

This patent is subject to a terminal disclaimer.

(21) Appl. No.: 12/689,548

(22) Filed: Jan. 19, 2010

(65) Prior Publication Data

US 2010/0124752 A1    May 20, 2010

Related U.S. Application Data

(63) Continuation of application No. 11/701,686, filed on Feb. 2, 2007, now Pat. No. 7,888,017.

(60) Provisional application No. 60/764,420, filed on Feb. 2, 2006.

(51) Int. Cl.
C12Q 1/68         (2006.01)
C12P 19/34        (2006.01)

(52) U.S. Cl.
CPC ......... *C12Q 1/6883* (2013.01); *C12Q 1/6809* (2013.01); *C12Q 1/6851* (2013.01); *C12Q 1/6858* (2013.01); *C12Q 1/6881* (2013.01); *C12Q 2600/156* (2013.01); *C12Q 2600/158* (2013.01); *Y10T 436/143333* (2015.01)

(58) Field of Classification Search
CPC ...................... C12Q 2565/50; C12Q 2565/518
See application file for complete search history.

(56) References Cited

U.S. PATENT DOCUMENTS

| | | | |
|---|---|---|---|
| 5,432,054 A | 7/1995 | Saunders et al. | |
| 5,641,628 A | 6/1997 | Bianchi | |
| 5,695,934 A | 12/1997 | Brenner | |
| 5,879,883 A | 3/1999 | Benson et al. | |
| 6,100,029 A | 8/2000 | Lapidus et al. | |
| 6,143,496 A | 11/2000 | Brown et al. | |
| 6,214,558 B1 | 4/2001 | Shuber et al. | |
| 6,258,540 B1 | 7/2001 | Lo et al. | |
| 6,391,559 B1 | 5/2002 | Brown et al. | |
| 6,440,705 B1 | 8/2002 | Stanton, Jr. et al. | |
| 6,440,706 B1 | 8/2002 | Vogelstein et al. | |
| 6,566,101 B1 | 5/2003 | Shuber et al. | |
| 6,632,655 B1 | 10/2003 | Mehta et al. | |
| 6,664,056 B2 | 12/2003 | Lo et al. | |
| 6,753,147 B2 | 6/2004 | Vogelstein et al. | |
| 6,927,028 B2 | 8/2005 | Dennis et al. | |
| 6,960,437 B2 | 11/2005 | Enzelberger et al. | |
| 7,332,277 B2 | 2/2008 | Dhallan | |
| 7,442,506 B2 | 10/2008 | Dhallan | |
| 7,476,363 B2 | 1/2009 | Unger et al. | |
| 7,645,576 B2 | 1/2010 | Lo et al. | |
| 7,655,399 B2 | 2/2010 | Cantor et al. | |
| 7,727,720 B2 | 6/2010 | Dhallan et al. | |
| 7,838,647 B2 | 11/2010 | Hahn et al. | |
| 7,888,017 B2* | 2/2011 | Quake et al. | 435/6.12 |
| 8,008,018 B2 | 8/2011 | Quake et al. | |
| 8,293,470 B2* | 10/2012 | Quake et al. | 435/6.11 |
| 2001/0051341 A1 | 12/2001 | Lo et al. | |
| 2002/0164816 A1 | 11/2002 | Quake | |
| 2003/0022207 A1 | 1/2003 | Balasubramanian et al. | |
| 2003/0044388 A1 | 3/2003 | Dennis et al. | |
| 2003/0186255 A1 | 10/2003 | Williams et al. | |
| 2003/0204331 A1 | 10/2003 | Whitney et al. | |
| 2004/0037470 A1 | 2/2004 | Simske | |
| 2004/0096892 A1 | 5/2004 | Wang et al. | |
| 2004/0137470 A1 | 7/2004 | Dhallan | |
| 2004/0203037 A1 | 10/2004 | Lo et al. | |
| 2004/0209299 A1 | 10/2004 | Pinter et al. | |
| 2005/0003351 A1 | 1/2005 | Fejgin et al. | |
| 2005/0019792 A1 | 1/2005 | McBride et al. | |
| 2005/0037388 A1 | 2/2005 | Antonarakis et al. | |
| 2005/0129581 A1 | 6/2005 | McBride et al. | |

(Continued)

FOREIGN PATENT DOCUMENTS

EP    0994963 B1    5/2003
EP    2161347 A2    3/2010

(Continued)

OTHER PUBLICATIONS

Nelson et al Var Sanguinis. 2001.80:112-116.*
Giurato, et al., "An accurate pipeline for analysis of NGS data of small non-coding RNA". EMBnetJournal vol. 18, pp. 100-101 (2012).
Green, et al., "Analysis of one million base pairs of Neanderthal DNA", Nature, vol. 444, pp. 330-336 (2006).
Nannya, et al, "A robust algorithm for copy number detection using high-density oligonucleotide single nucleotide polymorphism genotyping arrays", Cancer Res. vol. 65, pp. 6071-6079 (2005).

(Continued)

*Primary Examiner* — Carla Myers
(74) *Attorney, Agent, or Firm* — Rothwell, Figg, Ernst & Manbeck, P.C.

(57) ABSTRACT

The present methods are exemplified by a process in which maternal blood containing fetal DNA is diluted to a nominal value of approximately 0.5 genome equivalent of DNA per reaction sample. Digital PCR is then be used to detect aneuploidy, such as the trisomy that causes Down Syndrome. Since aneuploidies do not present a mutational change in sequence, and are merely a change in the number of chromosomes, it has not been possible to detect them in a fetus without resorting to invasive techniques such as amniocentesis or chorionic villi sampling. Digital amplification allows the detection of aneuploidy using massively parallel amplification and detection methods, examining, e.g., 10,000 genome equivalents.

9 Claims, 5 Drawing Sheets

(56) References Cited

U.S. PATENT DOCUMENTS

| | | |
|---|---|---|
| 2005/0145496 A1 | 7/2005 | Goodsaid et al. |
| 2005/0164241 A1 | 7/2005 | Hahn et al. |
| 2005/0221341 A1 | 10/2005 | Shimkets et al. |
| 2005/0221373 A1 | 10/2005 | Enzelberger et al. |
| 2005/0252773 A1 | 11/2005 | McBride et al. |
| 2006/0046258 A1 | 3/2006 | Lapidus et al. |
| 2006/0051775 A1 | 3/2006 | Bianchi et al. |
| 2006/0121452 A1 | 6/2006 | Dhallan |
| 2006/0252068 A1 | 11/2006 | Lo et al. |
| 2006/0252071 A1 | 11/2006 | Lo et al. |
| 2006/0257896 A1 | 11/2006 | Pollock et al. |
| 2007/0059680 A1 | 3/2007 | Kapur et al. |
| 2007/0059710 A1 | 3/2007 | Luke et al. |
| 2007/0134658 A1 | 6/2007 | Bohmer et al. |
| 2007/0202525 A1 | 8/2007 | Quake et al. |
| 2007/0207466 A1 | 9/2007 | Cantor et al. |
| 2007/0212689 A1 | 9/2007 | Bianchi et al. |
| 2007/0238105 A1 | 10/2007 | Barrett et al. |
| 2007/0275402 A1 | 11/2007 | Lo et al. |
| 2008/0020390 A1 | 1/2008 | Mitchell et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton et al. |
| 2008/0071076 A1 | 3/2008 | Hahn et al. |
| 2008/0090239 A1 | 4/2008 | Shoemaker et al. |
| 2008/0096216 A1 | 4/2008 | Quake |
| 2008/0096766 A1 | 4/2008 | Lee |
| 2008/0113358 A1 | 5/2008 | Kapur et al. |
| 2008/0124721 A1 | 5/2008 | Fuchs |
| 2008/0138809 A1 | 6/2008 | Kapur et al. |
| 2008/0153090 A1 | 6/2008 | Lo et al. |
| 2008/0182261 A1 | 7/2008 | Bianchi |
| 2008/0193927 A1 | 8/2008 | Mann et al. |
| 2008/0213775 A1 | 9/2008 | Brody et al. |
| 2008/0220422 A1 | 9/2008 | Shoemaker et al. |
| 2008/0299562 A1 | 12/2008 | Oeth et al. |
| 2009/0029377 A1 | 1/2009 | Lo et al. |
| 2009/0087847 A1 | 4/2009 | Lo et al. |
| 2009/0170113 A1 | 7/2009 | Quake et al. |
| 2009/0170114 A1 | 7/2009 | Quake et al. |
| 2009/0280492 A1 | 11/2009 | Stoughton et al. |
| 2009/0291443 A1 | 11/2009 | Stoughton et al. |
| 2010/0094562 A1 | 4/2010 | Shohat et al. |
| 2010/0112575 A1 | 5/2010 | Fan et al. |
| 2010/0124752 A1 | 5/2010 | Quake et al. |
| 2010/0216151 A1 | 8/2010 | Lapidus et al. |
| 2010/0216153 A1 | 8/2010 | Lapidus et al. |
| 2010/0255493 A1 | 10/2010 | Quake et al. |
| 2010/0291572 A1 | 11/2010 | Stoughton et al. |
| 2011/0003293 A1 | 1/2011 | Stoughton et al. |
| 2012/0190018 A1 | 7/2012 | Struble et al. |
| 2012/0270739 A1 | 10/2012 | Rava et al. |

FOREIGN PATENT DOCUMENTS

| | | |
|---|---|---|
| WO | 00/58507 A1 | 10/2000 |
| WO | WO 03/020974 A2 | 3/2003 |
| WO | 03048295 | 6/2003 |
| WO | WO 2004/065629 A1 | 8/2004 |
| WO | 2005/010145 A2 | 2/2005 |
| WO | WO 2005/023091 A2 | 3/2005 |
| WO | WO 2005/118852 A2 | 12/2005 |
| WO | 2006010610 A2 | 2/2006 |
| WO | WO 2006/108101 A2 | 10/2006 |
| WO | 2007044091 A2 | 4/2007 |
| WO | WO 2007/075836 A2 | 7/2007 |
| WO | WO 2007/092473 A2 | 8/2007 |
| WO | WO 2007/132166 A2 | 11/2007 |
| WO | WO 2007/132167 A2 | 11/2007 |
| WO | 2009013492 A1 | 1/2009 |
| WO | 2009013496 A1 | 1/2009 |
| WO | 2009019455 A2 | 2/2009 |

OTHER PUBLICATIONS

Noonan, et al., "Sequencing and Analysis of Neanderthal Genomic DNA", Science vol. 314, pp. 1113-1118 (2006).
Seo, et al., "Four-color DNA sequencing by synthesis on a chip using photocleavable fluorescent nucleotides", Proc. Nat. Acad. Sci. vol. 102, No. 17, pp. 5926-5931 (2005).
Smith, et al., "Using quality scores and longer reads improves accuracy of Solexa read mapping", BMC Bioinformatics, vol. 9, 128, pp. 1-8 (2008).
Thornley, "Analysis of Trace Data from Fluorescence Based Sanger Sequencing", Thesis, University of London Imperial College of Science, Technology and Medicine Department of Computing, 1997.
Solexa, Biotechniques, 2007, Protocol Guide, 1 page.
Huse, et al., "Accuracy and quality of massively parallel DNA pyrosequencing", Genome Biology, 2007, vol. 8, Issue 7, Article R143.
Stolovitzky, et al., "Statistical analysis of MPSS measurements: Application to the study of LPS-activated macrophage gene expression," Proceedings of the National Academy of Sciences, vol. 102, No. 5, Feb. 1, 2005, pp. 1402-1407.
Meyers, et al., "Analysis of the transcription coplexity of Arabidopsis thaliana by massive parallel signature sequencing," Nature Biotechnology, vol. 22, No. 8, Aug. 1, 2004, pp. 1006-1011.
Extended Search Report dated Nov. 23, 2012 in European Application No. 12175754.6.
Leutwyler, K., Mapping Chromosomes 21, Scientific American, May 15, 2000.
Tettelin, T., et al., "The nucleotide sequence of *Saccharomyces cerevisiae* chromosome VII," Nature 1997, 387:81-84.
Zavala, A., et al., "Genomic GC content prediction in prokaryotes from a sample of genes," Gene 2005, 357(2):127-143.
International Search Report, International Application No. PCT/US 09/57136, Mar. 16, 2010.
Dhallan et al., "A non-invasive test for prenatal diagnosis based on fetal DNA present in maternal blood: a preliminary study," Lancet 369:474-481 (Feb. 2, 2007).
EPO Examination Report, Application No. 07 763 674.4, Dec. 21, 2010, 3 pp.
Satiroglu Tufan, N. Lale, et al., Analysis of Cell-Free Fetal DNA from Maternal Plasma and Serum Using a Conventional Multiplex PCR: Factors Influencing Success, Turk J Med Sci, 35 (2005) 85-92.
Maureen Martin, et al., "A Method for Using Serum or Plasma as a Source of DNA for HLA Typing," Human Immunology, 1992, vol. 33, 108-113.
Stuart L. Emanuel, et al., "Amplification of Specific Gene Products from Human Serum," GATA, 1993, vol. 10, No. 6, 144-146.
Y-M. D. Lo, et al., "Prenatal Sex Determination by DNA Amplification from Maternal Peripheral Blood," The Lancet, Dec. 9, 1989, 1363-1365.
Y-M. D. Lo, et al., "Detection of fetal RhD sequence from peripheral blood of sensitized RhD-negative pregnant women," British Journal of Haematology, 1994, vol. 87, 658-660.
Y. M. Dennis Lo, et al., "Presence of fetal DNA in maternal plasma and serum," The Lancet, Aug. 16, 1997, vol. 350, 485-487.
Jouni Uitto, et al., "Probing the fetal genome: progress in non-invasive prenatal diagnosis," Trends in Molecular Medicine, Aug. 2003, vol. 9, No. 8, 339-343.
Sinuhe Hahn, et al., "Prenatal Diagnosis Using Fetal Cells and Cell-Free Fetal DNA in Maternal Blood: What is Currently Feasible?" Clinical Obstetrics and Gynecology, Sep. 2002, vol. 45, No. 3, 649-656.
Barbara Pertl, et al., "Fetal DNA in Maternal Plasma: Emerging Clinical Applications," Obstetrics and Gynecology, Sep. 2001, vol. 98, No. 3, 483-490.
Leo L.M. Poon, et al., "Circulating fetal DNA in maternal plasma," Clinical Chimica Acta, 2001, vol. 313, 151-155.
Y-M. D. Lo, et al., "Fetal DNA in Maternal Plasma," Ann. N. Y. Acad. Sci., Apr. 2000, vol. 906, 141-147.
Y-M. D. Lo, et al., "Detection of single-copy fetal DNA sequence from maternal blood," The Lancet, Jun. 16, 1990, vol. 335, 1463-1464.

(56) References Cited

OTHER PUBLICATIONS

Fiona M. F. Lun, et al., "Microfluidics Digital PCR Reveals a Higher than Expected Fraction of Fetal DNA in Maternal Plasma," Clinical Chemistry, 2008, vol. 54, No. 10, 1664-1672.
Young Ho Yang, et al., "Rapid Prenatal Diagnosis of Trisomy 21 by Real-time Quantitative Polymerase Chain Reaction with Amplification of Small Tandem Repeats and S100B in Chromosome 21," Yonsei Medical Journal, 2005, vol. 46, No. 2, 193-197.
Vincenzo Cirigliano, et al., "Clinical application of multiplex quantitative fluorescent polymerase chain reaction (QF-PCR) for the rapid prenatal detection of common chromosome aneuploidies," Molecular Human Reproduction, 2001, vol. 7, No. 10, 1001-1006.
Rebecca Sparkes, et al., "New Molecular Techniques for the Prenatal Detection of Chromosomal Aneuploidy," JOGC, Jul. 2008, No. 210, 617-621.
Y.M. Dennis Lo, et al., "Digital PCR for the molecular detection of fetal chromosomal aneuploidy," PNAS, Aug. 7, 2007, vol. 104, No. 32, 13116-13121.
Haissam Rahil, et al., Rapid detection of common autosomal aneuploidies by quantitative fluorescent PCR on uncultured amniocytes, European Journal of Human Genetics, 2002, vol. 10, 462-466.
Bernhard Zimmermann, "Molecular Diagnosis in Prenatal Medicine," Ph.D. Thesis, 2004.
Yuk-Ming Dennis Lo, "Noninvasive prenatal detection of fetal chromosomal aneuploidies by maternal plasma nucleic acid analysis: a review of the current state of the art," BJOG, 2009, vol. 116, 152-157.
Jay Shendure, et al., "Next-generation DNA sequencing," Nature, 2008, vol. 26, No. 10, 1135-1145.
H. Christina Fan, et al., "Noninvasive diagnosis of fetal aneuploidy by shotgun sequencing DNA from maternal blood," PNAS, Oct. 21, 2008, vol. 105, 16266-16271.
Richard A. White III, et al., "Digital PCR provides sensitive and absolute calibration for high throughput sequencing," BMC Genomics, Mar. 19, 2009, 10:116.
Frank Diehl, et al., "Digital quantification of mutant DNA in cancer patients," Curr Opin Oncol, 2007, 19:36-42.
P.J. Sykes, et al., "Quantitation of Targets for PCR by Use of Limiting Dilution," BioTechniques, 1992, vol. 13, No. 3, 444-449.
B. Zimmermann, et al., "Novel Real-Time Quantitative PCR Test for Trisomy 21," Jan. 1, 2002, Clinical Chemistry, American Association for Clinical Chemistry, vol. 48, No. 2, 362-363.
Ying Li, et al., "Size Separation of Circulatory DNA in Maternal Plasma Permits Ready Detection of Fetal DNA Polymorphisms," 2004, Clinical Chemistry, vol. 50, No. 6, 1002-1001.
H. Christina Fan, et al., "Detection of Aneuploidy with Digital Polymerase Chain Reaction," Analytical Chemistry, Oct. 1, 2007, vol. 79, No. 19, 7576-7579.
H. Christina Fan, et al., "Microfluidic digital PCR enables rapid prenatal diagnosis of fetal aneuploidy," American Journal of Obstetrics & Gynecology, May 2009, 543e1-543-e7.
EPO Search Report, 07 763 674.4, Jul. 31, 2009.
International Search Report and Written Opinion for PCT/US2007/003209, received Sep. 22, 2008.
Pohl et al., Principle and applications of digital PCR, Expert Reviews in Molecular Diagnosis. 2004.4: 41-47.
Chan et al., Size Distributions of Maternal and Fetal DNA in Maternal Plasma, Clinical Chemistry. 2004. 50: 88-92.
Sean Maloney, et al., "Microchimerism of maternal origin persists into adult life," Journal of Clinical Investigation, Jul. 1999, vol. 104, No. 1, 41-47.
M. Nelson, et al., "Genotyping fetal DNA by non-invasive means: extraction from maternal plasma," Vox Sanguinis, 2001, vol. 80, 112-116.
"Separation of RNA & DNA by Gel Filtration Chromatography," Edvotek, 1987, 1-9.

Tetsuya S. Tanaka, et al., "Genome-wide expression profiling of mid-gestation placenta and embryo using a 15,000 mouse developmental cDNA microarray," PNAS, Aug. 2000, vol. 97, No. 16, 9127-9132.
Y. M. Dennis Lo, et al., "Prenatal diagnosis: progress through plasma nucleic acids," Nature, Jan. 2007, vol. 8, 71-76.
Ryo Kimura, et al., "The DYRK1A gene, encoded in chromosome 21 Down syndrome critical region, bridges between b-amyloid production and tau phosphorylation in Alzheimer disease," Human Molecular Genetics, Nov. 29, 2006, vol. 16, No. 1, 15-23.
Joshua S. Marcus, et al., "Microfluidic Single-Cell mRNA Isolation and Analysis," American Chemical Society, Mar. 2006, p. A-F.
Y. M. Dennis Lo, et al., "Plasma placental RNA allelic ratio permits noninvasive prenatal chromosomal aneuploidy detection," Nature Medicine, Jan. 2007, 1-6.
Joshua S. Marcus, et al., "Parallel Picoliter RT-PCR Assays Using Microfluidics," Analytical Chemistry, Feb. 1, 2006, vol. 78, No. 3, 956-958.
Elizabeth A. Ottesen, et al., "Microfluidic Digital PCR Enables Multigene Analysis of Individual Environmental Bacteria," Science, Dec. 2006, vol. 314, 1464-1467.
Jong Wook Hong, et al., "Molecular biology on a microfluidic chip," Journal of Physics: Condensed Matter, 2006, vol. 18, S691-S701.
Y.M. Dennis Lo, et al., "Quantitative Analysis of Fetal NA in Maternal Plasma and Serum: Implications for Noninvasive Prenatal Diagnosis," Am J. Hum. Genet., 1998, vol. 62, 768-775.
Bert Vogelstein, et al., "Digital PCR," Proc. Natl. Acad. Sci. USA, Aug. 1999, vol. 96., 9236-9241.
Rossa W.K. Chiu, et al., "Effects of Blood-Processing Protocols on Fetal and Total DNA Quantification in Maternal Plasma," Clinical Chemistry, 2001, vol. 47, No. 9, 1607-1613.
Ilona Hromadnikova, et al., "Quantitative analysis of DNA levels in maternal plasma in normal and Down syndrome pregnancies," Bio Med Central, May 2002, 1-5.
Enders K.O. Ng, et al., "The Concentration of Circulating Corticotropin-releasing Hormone mRNA in Maternal Plasma Is Increased in Preeclampsia," Clinical Chemistry, 2003, vol. 49, No. 5, 727-731.
Ido Braslavsky, et al., "Sequence information can be obtained from single DNA molecules," PNAS, Apr. 2003, vol. 100, No. 7, 3960-3964.
Jun Zhu, et al., "Single Molecule Profiling of Alternative Pre-mRNA Splicing," Science, Aug. 2003, vol. 301, 836-838.
Devin Dressman, et al., "Transforming single DNA molecules into fluorescent magnetic particles for detection and enumeration of genetic variations," PNAS, Jul. 2003, vol. 100, No. 15, 8817-8822.
Eugene Y. Chan, et al., "DNA Mapping Using Microfluidic Stretching and Single-Molecule Detection of Fluorescent Site-Specific Tags," Genome Research, 2004, vol. 14, 1137-1146.
Al Sheng Xiong, et al., "A simple, rapid, high-fidelity and cost-effective PCR-based two-step DNA synthesis method for long gene sequences," Nucleic Acids Research, Apr. 19, 2004, vol. 32, No. 12, e98.
Grundevik, et al., "Molecular diagnostics of Aneuploidies", Chalmers University of Technology, Sweden, Department of Molecular Biotechnology, May 17, 2005, 12 pages.
Feinberg, et al, "A Technique for Radiolabeling DNA Restriction Endonuclease Fragments to High Specific Activity", Analytical Biochemistry, 132, 6-13 (1983).
Sequenom, Inc. and Sequenom Center for Molecular Medicine LLC's Patent L. R. 3-3 Preliminary Invalidity Contentions for U.S. Pat. Nos. 7,888,017, 8,008,018 and 8,195,415 and Patent L. R. 3-4 Document Production, *Verinata Health* v. *Sequenom*, No. 12-00865 (N.D. Cal. 2012), dated Sep. 28, 2012.
Sequenom, Inc. and Sequenom Center for Molecular Medicine LLC's Patent L. R. 4-2 Preliminary Claim Constructions and Extrinsic Evidence, *Verinata Health* v. *Sequenom*, No. 12-00865 (N.D. Cal. 2012), dated Oct. 26, 2012.
Chiu, et al. Non-invasive prenatal assessment of trisomy 21 by multiplexed maternal plasma DNA sequencing: large scale validity study. BMJ. Jan. 11, 2011;342:c7401. doi: 10.1136/bmj.c7401.

(56) References Cited

OTHER PUBLICATIONS

Chiu, et al. Noninvasive prenatal diagnosis of fetal chromosomal aneuploidy by massively parallel genomic sequencing of DNA in maternal plasma. Proc Natl Acad Sci U S A. Dec. 23, 2008;105(51):20458-63.
European Search Opinion dated Jul. 31, 2009 for EP07763674.4.
European search report dated Nov. 9, 2009 for Application No. 7784442.1.
European search report dated Dec. 21, 2009 for Application No. 07798579.4.
European search report dated Dec. 22, 2009 for Application No. 07798580.2.
European search report dated Dec. 22, 2009 for Application No. 07784444.7.
Hong, et al. A nanoliter-scale nucleic acid processor with parallel architecture. Nat. Biotechnol. 2004; 22(4):435-9.
International preliminary report on patentability dated Oct. 29, 2008 for PCT/US2007/003209.
Kasakov, et al. Extracellular DNA in the blood of pregnant women. Tsitologiia. 1995;37(3):232-6. (English translation only).
Office action dated Dec. 3, 2008 for U.S. Appl. No. 11/763,426 with pending claims.
Office Action dated Jan. 12, 2009 for U.S. Appl. No. 11/763,133 with pending claims.
Office action dated Mar. 4, 2009 for U.S. Appl. No. 11/228,454 with pending claims.
Office action dated Jul. 10, 2009 for U.S. Appl. No. 11/763,421 with pending claims.
Office action dated Sep. 23, 2009 for EP Application No. EP07763674.4 with pending claims.
Office action dated Nov. 3, 2009 for U.S. Appl. No. 11/763,133 with pending claims.
Office action dated Dec. 1, 2009 for U.S. Appl. No. 11/763,426 with pending claims.
Office action dated Dec. 31, 2009 for U.S. Appl. No. 11/763,421 with pending claims.
Office action dated Mar. 11, 2010 for U.S. Appl. No. 11/763,245 with pending claims.
Office action dated Jun. 14, 2010 for U.S. Appl. No. 11/763,426 with pending claims.
Office action dated Feb. 15, 2011 for U.S. Appl. No. 11/763,426 with pending claims.
Office action dated Mar. 29, 2011 for U.S. Appl. No. 11/763,245 with pending claims.
Office action dated May 6, 2011 for U.S. Appl. No. 11/763,133 with pending claims.
Office action (Ex parte Quayle) dated May 13, 2011 for U.S. Appl. No. 11/763,421 with pending claims.
Office action dated May 18, 2011 for U.S. Appl. No. 12/413,467 with pending claims.
Sehnert, et al. Optimal Detection of Fetal Chromosomal Abnormalities by Massively Parallel DNA Sequencing of Cell-Free Fetal DNA from Maternal Blood. Clin Chem. Apr. 25, 2011. [Epub ahead of print].
Solexa Genome Analysis System. 2006; 1-2.
Voelkerding, et al. Digital fetal aneuploidy diagnosis by next-generation sequencing. Clin Chem. Mar. 2010;56(3):336-8.
Bianchi, et al., "Isolation of fetal DNA from nucleated erythrocytes in maternal blood," Proc. Natl. Acad. Sci. USA, vol. 87, pp. 3279-3283 (May 1990).
Bischoff, et al., "Cell-free fetal DNA and intact fetal cells in maternal blood circulation: implications for first and second trimester non-invasive prenatal diagnosis," Human Reproduction Update, vol. 8, No. 6, pp. 493-500 (2002).
Brown, et al., "Chemical Synthesis and Cloning of a Tyrosine tRNA Gene," Methods in Enzmol., vol. 68, pp. 109-151 (1979).
Bruch, et al., "Trophoblast-like cells sorted from peripheral maternal blood using flow cytometry: A multiparametric study involving transmission electron microscopy and fetal DNA amplification," Prenatal Diagnosis, vol. 11, pp. 787-798 (1991).

Bustin, et al., "Pitfalls of Quantitative Real-Time Reverse-Transcription Polymerase Chain Reaction," J. Biomol. Tech., vol. 15, Issue No. 3, pp. 155-166 (Sep. 2004).
Chang, et al., "Assessment of Plasma DNA Levels, Allelic Imbalance, and CA 125 as Diagnostic Tests for Cancer," Journal of the National Cancer Institute, vol. 94, No. 22, pp. 1697-1703 (Nov. 20, 2002).
Dhallan, et al., "Methods to Increase the Percentage of Free Fetal DNA Recovered From the Maternal Circulation," J. Am. Med. Assoc., vol. 291, No. 9, pp. 1114-1119 (Mar. 3, 2004).
Fuscoe, et al., "An Efficient Method for Selecting Unique-Sequence Clones from DNA Libraries and Its Application to Fluorescent Staining of Human Chromosome 21 Using in Situ Hybridization," Genomics, vol. 5, pp. 100-109 (1989).
Gardiner, et al., "Analysis of human chromosome 21: correlation of physical and cytogenetic maps; gene and CpG island distributions," The EMBO Journal, vol. 9, No. 1, pp. 25-34 (1990).
Herzenberg, et al., "Fetal cells in the blood of pregnant women: Detection and enrichment by fluorescence-activated cell sorting," Proc. Natl. Acad. Sci., vol. 76, No. 3, pp. 1453-1455 (Mar. 1979).
Hesser, et al., "Down syndrome critical region protein 1 (DSCR1), a novel VEGF target gene that regulates expression of inflammatory markers on activated endothelial cells," Blood, vol. 104, No. 1, pp. 149-158 (Jul. 1, 2004).
Huber, et al., "High-resolution liquid chromatography of DNA fragments on non-porous poly(styrene-divinylbenzene) particles," Nucleic Acids Res., vol. 21, No. 5, pp. 1061-1066 (1993).
Kaiser, "An Earlier Look at Baby's Genes," Science, vol. 309, pp. 1476-1478 (Sep. 2, 2005).
Kato, et al., "A New Packing for Separation of DNA Restriction Fragments by High Performance Liquid Chromatography," J. Biochem., vol. 95, No. 1, pp. 83-86 (1984).
Li, et al., "Detection of Paternally Inherited Fetal Point Mutations for β-Thalassemia Using Size-Fractionated Cell-Free DNA in Maternal Plasma," J. Amer. Med. Assoc., vol. 293, No. 7, pp. 843-849 (Feb. 16, 2005).
Li, et al., "Size Separation of Circulatory DNA in Maternal Plasma Permits Ready Detection of Fetal DNA Polymorphisms," Clin. Chem., vol. 50, No. 6, pp. 1002-1011 (2004).
Mann, et al., "Strategies for the rapid prenatal diagnosis of chromosome aneuploidy," European Journal of Human Genetics, vol. 12, pp. 907-915 (2004).
Margulies, et al., "Genome sequencing in microfabricated high-density picolitre reactors," Nature, vol. 437, pp. 376-380 (Sep. 15, 2005).
Narang, et al., "Improved Phosphotriester Method for the Synthesis of Gene Fragments," Methods Enzmol., vol. 68, pp. 90-98 (1979).
Ng, et al., "mRNA of placental origin is readily detectable in maternal plasma," Proc. Nat. Acad. Sci., vol. 100, No. 8, pp. 4748-4753 (Apr. 15, 2003).
Ng, et al., "The Concentration of Circulating Corticotropin-releasing Hormone mRNA in Maternal Plasma Is Increased in Preeclampsia," Clin. Chem., vol. 49, No. 5, pp. 727-731 (2003).
Oudejans, et al., "Detection of Chromosome 21-encoded mRNA of Placental Origin in Maternal Plasma," Clinical Chemistry, vol. 49, No. 9, pp. 1445-1449 (2003).
Poon, et al., "Differential DNA Methylation between Fetus and Mother as a Strategy for Detecting Fetal DNA in Maternal Plasma," Clin. Chem., vol. 48, No. 1, pp. 35-41 (2002).
Shendure, et al., "Accurate Multiplex Polony Sequencing of an Evolved Bacterial Genome," Science, vol. 309, pp. 1728-1732 (Sep. 9, 2005).
Tong, et al., "Noninvasive Prenatal Detection of Fetal Trisomy 18 by Epigenetic Allelic Ratio Analysis in Maternal Plasma: Theoretical and Empirical Considerations," Clinical Chemistry, vol. 52, No. 12, pp. 2194-2202 (2006).
Warren, et al., "Transcription factor profiling in individual hematopoietic progenitors by digital RT-PCR," Proceedings of the National Academy of Sciences, vol. 103, No. 47, pp. 17807-17812 (Nov. 21, 2006).

(56) References Cited

OTHER PUBLICATIONS

Wong, et al., "Circulating Placental RNA in Maternal Plasma is Associated with a Preponderance of 5' mRNA Fragments: Implications for Noninvasive Prenatal Diagnosis and Monitoring," Clinical Chemistry, vol. 51, No. 10, pp. 1786-1795 (2005).

Yamada, et al., "PrimerStation: a highly specific multiplex genomic PCR primer design server for the human genome," Nucleic Acids Res., vol. 34, pp. W665-W669 (2006).

Zhou, et al., "Counting alleles reveals a connection between chromosome 18q loss and vascular invasion," Nature Biotechnology, vol. 19, pp. 78-81 (Jan. 2001).

Zhou, et al., "Counting alleles to predict recurrence of early-stage colorectal cancers," The Lancet, vol. 359, pp. 219-225 (Jan. 19, 2002).

Zimmerman, et al., QIAGEN News. Available via uri: <b2b.qiagen.com/literature/qiagennews/weeklyarticle/apr03/e12/default.aspx>, 2003, e12.

"A Safer Test for Down Syndrome", Technology Review, Oct. 7, 2008, 2 pages.

"DNA answer to Down's Screening", http://www.thenakedscientists.com/HTML/science-news/news/1492/, Oct. 12, 2008, 2 pages.

"New Blood Test for Down Syndrome", http://phys.org/news/2008-10-blood-syndrome.html, Oct. 7, 2008, 3 pages.

"New Prenatal Blood Test for Down Syndrome", http://www.medicalgeek.com/articles/13083-new-prenatal-blood-test-down-syndrome.html, Oct. 8, 2008, 2 pages.

Office action issued in U.S. Appl. No. 12/393,803, Apr. 25, 2011, 27 pages.

Chiu, et al., "Noninvasive Prenatal Diagnosis by Analysis of Fetal DNA in Maternal Plasma", Methods in Molecular Biology, 336, Clinical Applications of PCR, Second Edition, Edited by Y.M. Dennis Lo et al., Humana Press Inc., 2006, 101-109.

Juneau, et al., "Microarray-Based Cell-Free DNA Analysis Improves Noninvasive Prenatal Testing", Fetal Diagnosis and Therapy, DOI:10.1159/000367626, 2014.

Stewart, et al., "Non-invasive prenatal test for Down's syndrome developed", BioNews, Oct. 13, 2008, 4 pages.

\* cited by examiner

Chr 12 HEX

NON-INVASIVE FETAL GENETIC SCREENING BY DIGITAL ANALYSIS

CROSS-REFERENCE TO RELATED APPLICATIONS

This application claims priority from U.S. Provisional Patent Application No. 60/764,420 filed on Feb. 2, 2006, and U.S. Utility patent application Ser. No. 11/701,686, filed Feb. 2, 2007, which are hereby incorporated by reference in their entirety.

STATEMENT OF GOVERNMENTAL SUPPORT

This invention was made with U.S. Government support under contract 0535870 awarded by the National Science Foundation. The U.S. Government has certain rights in this invention.

REFERENCE TO SEQUENCE LISTING

Applicants assert that the paper copy of the Sequence Listing is identical to the Sequence Listing in computer readable form found on the accompanying computer file. Applicants incorporate the contents of the sequence listing by reference in its entirety.

BACKGROUND OF THE INVENTION

Field of the Invention

The present invention relates to the field of fetal genetic screening and to the field of quantitative nucleic acid analysis.

Related Art

It is now recognized that fetal DNA sheds from the placenta and mixes with the mother's blood at fairly high levels—between 3% and 6% of DNA in the mother's blood is from the fetus. This observation has been used in conjunction with PCR assays for a variety of fetal genetic screens—gender, Rh, and thalassemia. However, the technique remains limited for two primary reasons: first, the PCR assays trade off sensitivity for specificity, making it difficult to identify particular mutations, and second, the most common genetic disorder, Down Syndrome, is a chromosomal trisomy and therefore cannot be detected by conventional PCR in a mixed sample.

It has now been found that these problems can be solved by quantitative examination of large numbers of chromosome samples through the use of highly scalable techniques. This approach is termed here "digital analysis," and involves the separation of the extracted genomic material into discrete units so that the detection of a target sequence (e.g., chromosome 21) may be simply quantified as binary (0, 1) or simple multiples, 2, 3, etc. The primary example of a technique that can be used to yield such "digital" results is "digital PCR," which allows efficient amplification from single molecules, followed by subsequent quantitative analysis. Digital PCR, as the term is used here, refers to a quantitative, limited dilution of a nucleic acid sample, such as into multiwell plates, then the amplification of a nucleic acid molecule in a well, which due to the dilution, should be either 0 or 1 molecule. Digital PCR using multiwell plates has been used previously to detect rare mutations by either serial analysis of single molecule (i.e., clonal) amplicons (Vogelstein B, Kinzler K W. Proc Natl Acad Sci USA. 1999 Aug. 3; 96 (16): 9236-41) or by enhancing the sensitivity of differential amplification (www(dot)fluidigm.com/did-IFC.htm). Described below is an invention whereby digital PCR can be applied to noninvasive fetal diagnostics in order to detect fetal mutations with specificity and sensitivity beyond what is possible with conventional PCR analysis.

Furthermore, as also described in connection with the invention described below, digital PCR can be used to detect aneuploidy, such as the trisomy that causes Down Syndrome. Since aneuploidies do not present a mutational change in sequence, and are merely a change in the number of chromosomes, it has not been possible to detect them in a fetus without resorting to invasive techniques such as amniocentesis or chorionic villi sampling (Science 309, 2 Sep. 2005 pp. 1476-8).

Another form of digital PCR has been described as emulsion PCR, which has been used to prepare small beads with clonally amplified DNA—in essence, each bead contains one amplicon of digital PCR. (Dressman et al, Proc Natl Acad Sci USA. 100, 8817 (Jul. 22, 2003)).

Another form of Digital PCR can be carried out using microfluidics. In this embodiment, described below, DNA is diluted and separated into small, discrete samples for forming reaction samples by a series of channels and valves.

An example of a suitable method for single molecule analysis that may be adapted to the present methods is given in Braslaysky et al., "Sequence information can be obtained from single DNA molecules, *Proc. Nat. Acad. Sci.* 100(7): 3960-3964 (2003), which uses sequential incorporation of labeled nucleotides onto an immobilized single stranded DNA template and monitoring by fluorescent microscopy.

Another aspect of the relevant art involves sample preparation in order to carry out the present processes. That is, the fetal DNA may be enriched relative to maternal DNA. Chan, et al., "Size Distribution of Maternal and Fetal DNA in Maternal Plasma," *Clin. Chem.* 50(1): 88-92 (2004) reports that plasma DNA molecules are mainly short DNA fragments. The DNA fragments in the plasma of pregnant women are significantly longer than DNA fragments from non-pregnant women, and longer than fetal DNA.

Related Publications and Patents

Vogelstein et al., "Digital Amplification," U.S. Pat. No. 6,440,706, issued Aug. 27, 2002, discloses the identification of pre-defined mutations expected to be present in a minor fraction of a cell population.

Lo, "Fetal DNA in Maternal Plasma: Biology and Diagnostic Applications," *Clin. Chem.* 46:1903-1906 (2000) discloses the demonstration of fetal DNA in maternal plasma. The authors found a mean fractional level of 3.4% fetal DNA in maternal DNA in plasma during early pregnancy. The authors report detection of the RhD gene and microsatellite polymorphisms in the plasma of pregnant women.

Li et al., "Detection of Paternally Inherited Fetal Point Mutations for β-Thalassemia Using Size Fractionated Cell-Free DNA in Maternal Plasma," *J. Amer. Med. Assoc.* 293:843-849 (Feb. 16, 2005) discloses that the analysis of cell-free fetal DNA in maternal plasma has proven to be remarkably reliable for the assessment of fetal loci absent from the maternal genome, such as Y-chromosome specific sequences or the RhD gene in pregnant women who are Rh-negative. The authors report on the extraction and size fractionation of maternal plasma DNA using agarose gel electrophoresis. Then, peptide-nucleic acids (PNA) were used to bind specifically to a maternal allele to suppress PCR amplification of the of the wild type maternal allele, thereby enriching for the presence of paternally inherited mutant sequences. Four distinct point mutations in the β-globin gene were examined. It was found that the PNA step was necessary for the detection of mutant alleles using allele specific PCR.

Lo et al., "Quantitative Analysis of Fetal DNA in Maternal Plasma and Serum: Implications for Noninvasive Prenatal Diagnosis," *Am. J. Hum. Genet.* 62:768-775 (1998) discloses a real-time quantitative PCR assay to measure the concentration of fetal DNA in maternal plasma and serum. The authors found a mean of 25.4 genome equivalents/ml of fetal DNA in early pregnancy. This corresponds to about 3.4% of total DNA in early pregnancy.

Chan et al., "Size Distribution of Maternal and Fetal DNA in Maternal Plasma," *Clin. Chem.* 50:89-92 (January 2004) investigated the size distribution of plasma DNA in non-pregnant women and pregnant women, using a panel of quantitative PCR assays with different amplicon sizes targeting the leptin gene. They found that the DNA fragments in the plasma of pregnant women are significantly longer than those in the plasma of non-pregnant women, and the maternal-derived DNA molecules are longer than the fetal-derived ones.

Tufan et al., "Analysis of Cell-Free Fetal DNA from Maternal Plasma and Serum Using a Conventional Multiplex PCR: Factors Influencing Success," *Turk. J. Med. Sci.* 35: 85-92 (2005) compared the success rates of two different DNA extraction techniques, the heat based direct method and the QIAMP DNA blood mini kit method. The crucial role of PCR optimization was also reported. The authors used the DYS14 marker for the Y chromosome and the GAPH gene for a control. The QIAMP mini kit was found to give the best results in sex determination analysis using multiplex PCR and ethidium bromide staining on gels.

Hromadnikova et al., "Quantitative analysis of DNA levels in maternal plasma in normal and Down Syndrome pregnancies," *BMC Pregnancy and Childbirth* 2(4): 1-5 (2002), investigated total DNA levels in maternal plasma and found no difference in fetal DNA levels between the patients carrying Down Syndrome fetuses and the controls. Real time quantitative PCR analysis was performed using primers to the β-globin gene and the SRY locus.

Grundevikk and Rosen, "Molecular Diagnosis of Aneuploidies," published on line at www(dot)molbiotech.chalmers.se/research/mk/mbtk/Molecular%20diagnostics%20of%20aneupl oidies%20-%20rapport.pdf, suggests that non-invasive methods for detection of aneuploidies (such as Down Syndrome, Edwards Syndrome or extra sex chromosomes) may be carried out on fetal nucleated cells isolated from maternal blood. In their review, the authors also describe quantitative fluorescence polymerase chain reaction (QF-PCR), based on amplification of short tandem repeats specific for the chromosome to be tested. They describe tests where DNA was amplified from amniotic or chorionic villus samples. The authors suggest that the STR markers will give PCR products of different size, and these size differences may be studied by analyzing peak sizes in electrophoresis. It is also proposed that quantitative real time PCR may be used to diagnose Down Syndrome by comparing the amount of a gene located on chromosome 12 to the amount of a gene located on another autosomal chromosome. If the ratio of these two genes is 1:1, the fetus is normal, but if the ratio of these genes is 3:2, it indicates Down Syndrome. The authors propose the use of Down Syndrome marker DSCR3. They also suggest that the housekeeping gene GAPDH on chromosome 12 can be used as a reference.

Poon et al., "Differential DNA Methylation between Fetus and Mother as a Strategy for Detecting Fetal DNA in Maternal Plasma," *Clin. Chem.* 48(1): 35-41 discloses the detection of genes or mutations in a fetus where the same mutation or condition is also present in maternal DNA. That is, the use of fetal DNA in maternal plasma is limited due to the low amount of fetal DNA compared to maternal DNA. The authors overcame this limitation by detecting the IGF2-H19 locus, which is maintained in a methylated DNA status in the paternal allele and is unmethylated in the maternal allele. The authors used a bisulfite modification kit whereby unmethylated cytosine residues were converted to uracil. The sequence difference between methylated and unmethylated DNA sequences could be distinguished with different PCR primers. DNA extracted from buffy coat was used.

Science 309:1476 (2 Sep. 2005) News Focus "An Earlier Look at Baby's Genes" describes attempts to develop tests for Down Syndrome using maternal blood. Early attempts to detect Down Syndrome using fetal cells from maternal blood were called "just modestly encouraging." The report also describes work by Dennis Lo to detect the Rh gene in a fetus where it is absent in the mother. Other mutations passed on from the father have reportedly been detected as well, such as cystic fibrosis, beta-thalassemia, a type of dwarfism and Huntington's disease. However, these results have not always been reproducible.

United States Patent Application 20040137470 to Dhallan, Ravinder S, published Jul. 15, 2004, entitled "Methods for detection of genetic disorders," describes a method for detecting genetic disorders using PCR of known template DNA and restriction analysis. Also described is an enrichment procedure for fetal DNA. It also describes a method used to detect mutations, and chromosomal abnormalities including but not limited to translocation, transversion, monosomy, trisomy, and other aneuploidies, deletion, addition, amplification, fragment, translocation, and rearrangement. Numerous abnormalities can be detected simultaneously. The method is said to provide a non-invasive method to determine the sequence of fetal DNA from a tissue, such as blood, drawn from a pregnant female, and a method for isolating free nucleic acid from a sample containing nucleic acid.

BRIEF SUMMARY OF THE INVENTION

The following brief summary is not intended to include all features and aspects of the present invention, nor does it imply that the invention must include all features and aspects discussed in this summary.

Briefly, the present invention is directed to a method of differential detection of target sequences in a mixture of maternal and fetal genetic material. One obtains maternal tissue containing both maternal and fetal genetic material. Preferably, the maternal tissue is maternal peripheral blood or blood plasma. The term "plasma" may include plasma or serum. The genetic material may be genomic DNA or RNA, preferably mRNA. In the case of mRNA, one may choose target sequences corresponding to genes that are highly expressed in the placenta for fetal genetic material. The genetic material (e.g., DNA) in each reaction sample is detected with a sequence specific reactant directed to at least one of two target sequences in the genetic material to obtain a detectable reaction product if the target sequence is present in the reaction sample. For example, a probe specific to chromosome 21 is bound to the reaction sample, along with a control probe specific to another chromosome. In most cases, the results will be from maternal DNA, but a small number of results will be obtained from fetal DNA. In order to distinguish random variation from fetal results, a large number of reactions are run, and statistical methods are applied to the results. The labeling and detection in the present method is used to distinguish the presence or absence of a single target sequence, referred to as "digital analysis," although it may be performed with sensitive nucleic acid detection methods which distinguish between one and more than one target sequence in a discrete sample. Many fluorescent techniques have this sensitivity. The target sequences are chosen so that a maternal sequence and a fetal sequence are distinguishable, such as two copies of a maternal sequence versus two copies of a fetal sequence.

The genetic material thus obtained is distributed into discrete samples, where each sample will contain, on average not more than about one target sequence per sample. The average of one target sequence means that, for practical reasons, the sample will contain, preferably 0.1 to 0.8 genome equivalents per discrete sample, ideally 0.5 genome equivalent per sample. The method may be performed with dilutions whereby more target sequences are detected in samples containing a trisomic or increased copy number of target sequence. That is, if one is analyzing chromosome 21, the mixture may be diluted such that, on average, one may detect two chromosomes present in a maternal DNA, and three chromosomes in a Down Syndrome fetal DNA. Alternatively, the method may be performed with dilutions whereby more reaction samples are positive in this situation. The presence or absence of different target sequences in the discrete samples is detected; and the results are analyzed whereby the number of results from the discrete samples will provide data sufficient to obtain results distinguishing different target sequences. In one aspect, the method involves an analysis of a trisomy. In this method, one of the different target sequences (e.g. chromosome 21) is diploid in maternal genetic material and aneuploid in fetal genetic material and another of the different target sequences (e.g. chromosome 12) is diploid in both maternal and fetal genetic material.

The discrete samples are in reaction samples where the target sequences can be analyzed. The reaction samples may be, for example, wells in a microtiter plate, aqueous phases in an emulsion, areas in an array surface, or reaction chambers in a microfluidic device. The reaction samples may be used for PCR analysis of the discrete samples. The discrete samples are contacted with a plurality of PCR primers, including at least one (or one forward and one reverse) primer directed specifically to a maternal control sequence, expected to be the same in both mother and fetus. PCR primers are also directed specifically to a fetal sequence, i.e. one which may be present in both mother and fetus, but is amplified or altered in the fetus. PCR amplification will allow detection of these two different sequences, and, according to the present method, there will be a differential in the case of an abnormal fetal target sequence. The PCR method may be (but is not necessarily) quantitative. Quantitative real time PCR, which includes hybridizing target sequences with a nucleic acid having a fluorescent label, may be used. A fluorescent probe hybridizing to the target sequence may also be used. A number of "digital PCR" protocols are known for this purpose, as well as bead-based or emulsion PCR. While florescent probes are readily available and may be used to provide sensitive results, e.g., in FRET combinations, other labeling techniques may be used.

The number of discrete samples is chosen according to the results desired. In one aspect, it is preferred that a high degree of statistical significance is obtained, and the number of samples is at least about 10,000. In order to improve statistical confidence, it is preferable to employ large numbers of reactions, preferably between 500 and 100,000, more preferably between 10,000 and 100,000 or more reactions, depending on the percentage of fetal DNA present in the mixture. The results to be obtained should be statistically significant for purposes of the analysis conducted, e.g. initial screening, primary diagnosis, etc. A commonly used measure of statistical significance when a highly significant result is desired is $p<0.01$, i.e., a 99% confidence interval based on a chi-square or t-test.

However, as shown below, results can be obtained with less, e.g. on the order of about 500 samples, placed in separate reaction samples. Fewer discrete samples may be analyzed where the genetic material is present in a higher concentration in the mixture. The mixture may be enriched for fetal genetic material. One method to enrich plasma DNA for fetal DNA is size separation, whereby a preparation comprising only DNA fragments less than about 300 bp are used for measuring target sequences.

A variety of genetic abnormalities may be detected according to the present method, including known alterations in one or more of the genes: CFTR, Factor VIII (F8 gene), beta globin, hemachromatosis, G6PD, neurofibromatosis, GAPDH, beta amyloid, and pyruvate kinase. The sequences and common mutations of these genes are known. Other genetic abnormalities may be detected, such as those involving a sequence which is deleted in a human chromosome, is moved in a translocation or inversion, or is duplicated in a chromosome duplication, wherein said sequence is characterized in a known genetic disorder in the fetal genetic material not present in the maternal genetic material. For example chromosome trisomies may include partial, mosaic, ring, 18, 14, 13, 8, 6, 4 etc. A listing of known abnormalities may be found in the OMIM Morbid map, www(dot)ncbi.nlm.nih.gov/Omim/getmorbid.cgi.

In general, the term "aneuploidy" is used to refer to the occurrence of one or more extra or missing chromosomes.

In one aspect, the present method of differential detection of target sequences may involve direct sequencing of target sequences the genetic material. Single molecule sequencing, as is known, is further described below. The method may also comprise sequencing of amplified derivatives of the target sequences clones or amplicons of the genetic material. That is, a target sequence in a discrete sample is amplified by PCR, i.e. as an amplicon, or cloned into a vector that is grown up and thereby amplified by obtaining multiple copies of the vector insert.

In another aspect, the present invention comprises materials selected and combined for carrying out the present methods. Thus is provided a kit for differential detection of target sequences in maternal and fetal DNA in a mixed DNA sample, comprising primers specific for a genetically abnormal sequence and a control sequence, such as two chromosomes, one of which is possibly aneuploid and one of which is presumed diploid; a PCR reaction buffer for forming a PCR reaction sample with the primers in a device having separate reaction samples; and a size separation medium for separating the DNA sample into a fraction having less than about 1000 bp. The size separation medium may be gel or centrifugation material for recovering smaller DNA fragments and thus enriching fetal DNA. The kit may further comprise a pair of primers specific to chromosome 21. The kit may further comprise the device having separate reaction samples for discrete samples. The device may be a microfluidic device or a microtiter plate having at least 1,000 discrete reaction samples.

DETAILED DESCRIPTION OF THE PREFERRED EMBODIMENT

Outline
I. Overview
II. Description of Steps
   A. Tissue Preparation
   B. Distribution of DNA molecules
   C. Detection and Quantification
   1. Digital PCR Methods
   2. Bead emulsion PCR
   3. Microfluidic Dilution with PCR
   4. Single molecule detection and/or sequencing
   D. Quantitative evaluation
III. Specific applications
   A. Preparation for trisomy with frequency analysis.
   B Sample Protocol
IV. Examples

I. Overview

The methods and materials described below apply techniques for analyzing numerous nucleic acids contained in a tissue sample (preferably serum or, more preferably, plasma) containing a mixture of DNA from both the mother and the fetus, and allowing detection of small but statistically significant differences.

The present invention involves the analysis of maternal blood for a genetic condition, wherein the mixed fetal and maternal DNA in the maternal blood is analyzed to distinguish a fetal mutation or genetic abnormality from the background of the maternal DNA. It has been found that, using a combination of steps, a DNA sample containing DNA from both the mother and the fetus can be analyzed to distinguish a genetic condition present in a minor fraction of the DNA, which represents the fetal DNA. The method employs "digital analysis," in which the DNA in the sample is isolated to a nominal single target molecule in a small reaction volume. Each sample mixture has a possibility of having distributed in it less than 1 target (i.e., 0 target) or more than one target. Next, the target molecules are detected in each reaction well, preferably as target sequences which are amplified, which may include a quantization of starting copy number of the target sequence, that is, 0, 1, 2, 3, etc. A control sequence is used to distinguish an abnormal increase in the target sequence, e.g., a trisomy. Thus there is a differential detection of target sequences, one of which is chosen to represent a normal genotype present in both mother and offspring, and one of which is chosen for detection of an abnormal genotype in the offspring, where the target sequence in the offspring will be different from that of the mother, e.g. in trisomy.

Figure 1A:
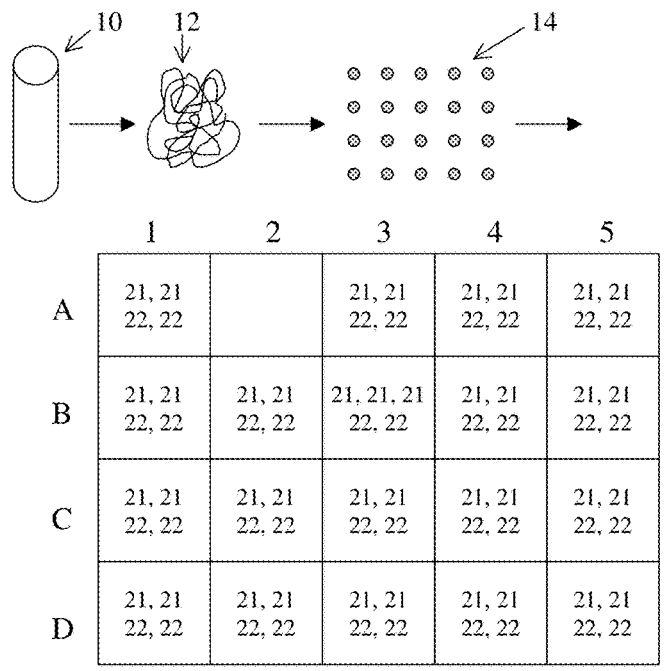
FIG. 1 is a schematic illustration of the present analytical method, showing distribution of genetic material into compartments (1A), chromosome peaks of different height (1B), and statistical analysis of chromosomes (1C)
Figure 1B:
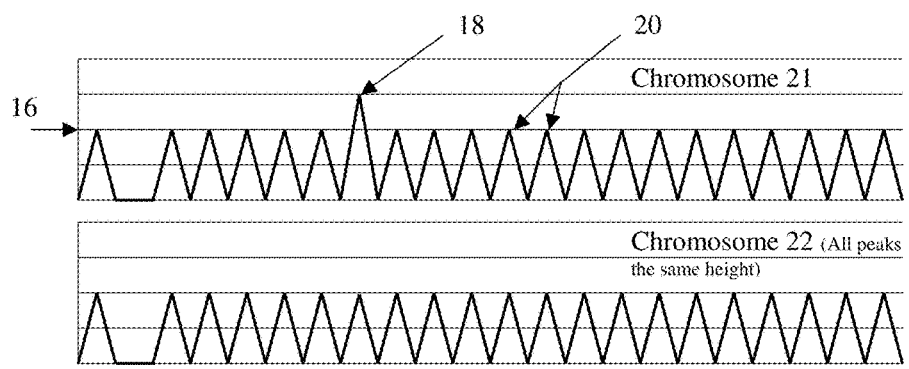

FIG. 1A illustrates an embodiment where quantitative detection, e.g. quantitative real time PCR, is used. Blood 10 is processed to obtain plasma DNA 12, which is diluted and distributed into aliquots 14. These are added to reactions wells 1A through 5D. Shown in the wells are targets representing chromosomes 21 and 22. In well 2A, no target DNA is found; some wells (not shown) may have excess DNA. In well 3B, fetal DNA having trisomy 21 (Down Syndrome) is found. The remainder of the wells contains maternal DNA. The DNA is amplified and/or labeled and a quantitative readout is obtained, as shown at 16. Peak 18 representing well 3B will be 50% higher than the peaks from the other well, or the peaks from a reference sequence on chromosome 22. Well A2, lacking either 21 or 22, will have no peak. The peaks are shown at 20. A single run will have numerous random variations, such as wells that have no target sequence, or have duplication through sample variability. Also, samples with no target will clearly result in no peak at all; wells with two or more targets, will give peaks significantly higher than peak 18, i.e., 2× or 2.5× controls. These results are distinguished by running a multitude of reactions, followed by statistical analysis that can discriminate random variations from true results.

Figure 1C:
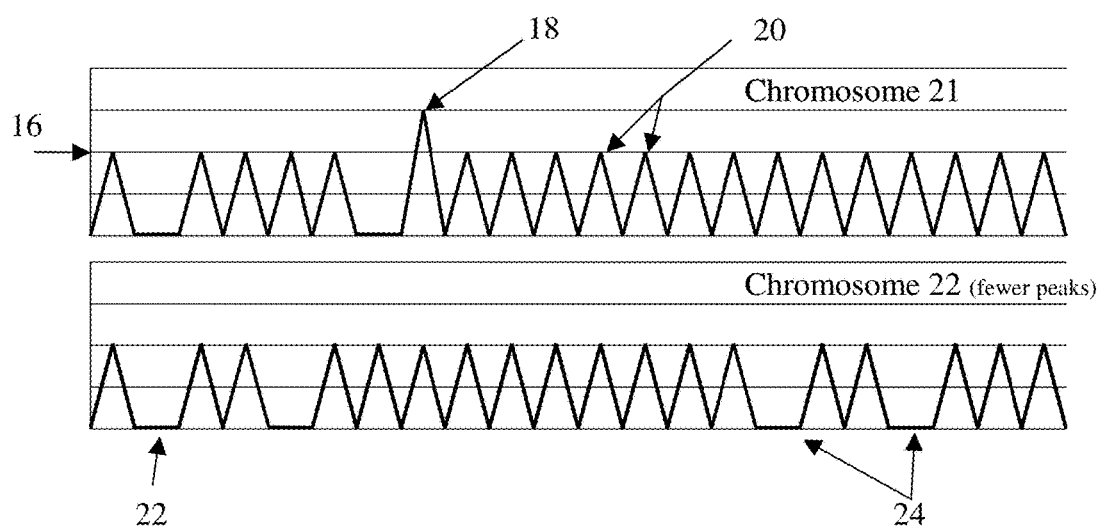

FIG. 1C illustrates an embodiment where the DNA is distributed in a more dilute fashion (less than 1, or about one half genome equivalents per well). In this case chromosome 21 labels (primers) will generate more positives than chromosome 22 (a diploid chromosome) specific labels (e.g., primers) due simply to the slightly greater abundance of chromosome 21 in a trisomy-containing sample. As shown, some wells will contain positives 20 for both chromosomes, some will contain negatives 22 for both chromosomes, but some will contain blanks 24 for the diploid chromosome and peaks for the trisomic chromosome, due to its greater abundance. The data from a higher peak 18 is not used in this mode. As explained below, this slight difference can be made statistically significant by examining a large number of wells, and by the sensitivity of the present method to a single molecule.

Thus, the present method comprises generally the following steps:

1. Obtaining a tissue containing DNA from a pregnant subject, which DNA is known to have about 3% fetal DNA. This material is preferably drawn blood, and the circulating DNA is found in the blood plasma, rather than in cells. The blood or plasma may optionally be enriched for fetal DNA by known methods, such as size fractionation to select for DNA fragments less than about 300 bp. Alternatively, maternal DNA, which tends to be larger than about 500 bp may be excluded. Another enrichment step may be to treat the blood sample with formaldehyde, as described in Dhallan et al. "Methods to Increase the Percentage of Free Fetal DNA Recovered From the Maternal Circulation," J. Am. Med. Soc. 291(9): 1114-1119 (March 2004).

2. Distributing single DNA molecules from this sample to a number of discrete reaction samples, where the number of reaction samples is selected to give a statistically significant result for the number of copies of a target in the DNA molecules. Further, the reaction sample is confined to a small volume to bring the reaction molecules into close approximation. The amount of DNA molecule per reaction sample is preferably on the order of one copy of the chromosome of interest equivalent per reaction sample.

3. Detecting the presence of the target in the DNA in a large number of reaction samples, preferably with a sequence specific technique such as highly multiplexed short read sequencing or a PCR reaction wherein the PCR product is labeled to give a convenient quantitative read out. The detection step is referred to here as "digital PCR" and may be carried out by a variety of methods, such as (a) by PCR on samples diluted into individual wells of a microtiter plate; (b) PCR on samples diluted into emulsions containing primers immobilized to beads; or (c) PCR on samples trapped in a microfluidic chamber; and 4. Quantitative analysis of the detection of the maternal and fetal target sequences. In some cases this may include targets to different regions, such as probes to a target on a chromosome suspected of being present in an abnormal copy number (trisonomy) compared to a normal diploid chromosome, which is used as a control.

II. Description of Steps

A. Tissue Preparation

The present method is directed to non-invasive testing. The preferred starting material is maternal peripheral venous blood. In order to obtain sufficient DNA for testing, it is preferred that 10-20 mL of blood be drawn, in order to obtain about at least 10,000 genome equivalents of total DNA. This sample size is based on an estimate of fetal DNA being present as roughly 25 genome equivalents/mL of maternal plasma in early pregnancy, and a fetal DNA concentration of about 3.4% of total plasma DNA. However, less blood may be drawn for a genetic screen where less statistical significance is required, or the DNA sample is enriched for fetal DNA.

It should be noted that, while the present description refers throughout to DNA, fetal RNA found in maternal blood may be analyzed as well. As described in Ng et al., "mRNA of placental origin is readily detectable in maternal plasma," Proc. Nat. Acad. Sci. 100(8): 4748-4753 (2003), hPL (human placental lactogen) and hCG (human chorionic gonadotropin) mRNA transcripts were detectable in maternal plasma, as analyzed using the respective real-time RT-PCR assays. In the present method, mRNA encoding genes expressed in the placenta and present on the chromosome of interest are used. For example, DSCR4 (Down syndrome critical region 4) is found on chromosome 21 and is mainly expressed in the placenta. Its mRNA sequence may be found at GenBank NM_005867. In this case, it is preferred to use RNase H minus (RNase H—) reverse transcriptases (RTs) to prepare cDNA for detection. RNase H— RTs are available from several manufacturers, with SuperScript™ II (Invitrogen) being the most widely used. Reverse transcriptase PCR may be used as described below for chromosomal DNA.

i. Enrichment of DNA or RNA from Plasma

The maternal blood may be processed to enrich the fetal DNA concentration in the total DNA, as described in Li et al., supra. Briefly, circulatory DNA is extracted from 5 to 10-mL maternal plasma using commercial column technology (Roche High Pure Template DNA Purification Kit; Roche, Basel, Switzerland) in combination with a vacuum pump. After extraction, the DNA is separated by agarose gel (1%) electrophoresis (Invitrogen, Basel, Switzerland), and the gel fraction containing circulatory DNA with a size of approximately 300 bp is carefully excised. The DNA is extracted from this gel slice by using an extraction kit (QIAEX II Gel Extraction Kit; Qiagen, Basel, Switzerland) and eluted into a final volume of 40-μL sterile 10-mM trishydrochloric acid, pH 8.0 (Roche).

DNA may be concentrated by known methods, including centrifugation and various enzyme inhibitors. The DNA is bound to a selective membrane (e.g., silica) to separate it from contaminants. The DNA is preferably enriched for fragments circulating in the plasma, which are less than 1000 base pairs in length, generally less than 300 bp. This size selection is done on a DNA size separation medium, such as an electrophoretic gel or chromatography material. Such a material is described in Huber et al., "High-resolution liquid chromatography of DNA fragments on non-porous poly(styrene-divinylbenzene) particles," *Nucleic Acids Res.* 1993 Mar. 11; 21(5): 1061-1066, gel filtration chromatography, TSK gel, as described in Kato et al., "A New Packing for Separation of DNA Restriction Fragments by High Performance Liquid Chromatography," *J. Biochem,* 1984, Vol. 95, No. 1 83-86.

In addition, enrichment may be accomplished by suppression of certain alleles through the use of peptide nucleic acids (PNAs), which bind to their complementary target sequences, but do not amplify.

Plasma RNA extraction is described in Enders et al., "The Concentration of Circulating Corticotropin-releasing Hormone mRNA in Maternal Plasma Is Increased in Preeclampsia," *Clinical Chemistry* 49: 727-731, 2003. As described there, plasma harvested after centrifugation steps is mixed Trizol LS reagent (Invitrogen) and chloroform. The mixture is centrifuged, and the aqueous layer transferred to new tubes. Ethanol is added to the aqueous layer. The mixture is then applied to an RNeasy mini column (Qiagen) and processed according to the manufacturer's recommendations.

ii. Blood—Extraction from Fetal Cells

United States Patent Application 20040137470 to Dhallan, Ravinder S, published Jul. 15, 2004, entitled "Methods for detection of genetic disorders," describes an enrichment procedure for fetal DNA," in which blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Agents that impede cell lysis or stabilize cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, etc. Any concentration of agent that stabilizes cell membranes or impedes cell lysis can be added. In a preferred embodiment, the agent that stabilizes cell membranes or impedes cell lysis is added at a concentration that does not impede or hinder subsequent reactions.

Flow cytometry techniques can also be used to enrich fetal cells (Herzenberg et al., PNAS 76: 1453-1455 (1979); Bianchi et al., PNAS 87: 3279-3283 (1990); Bruch et al., Prenatal Diagnosis 11: 787-798 (1991)). U.S. Pat. No. 5,432,054 also describes a technique for separation of fetal nucleated red blood cells, using a tube having a wide top and a narrow, capillary bottom made of polyethylene. Centrifugation using a variable speed program results in a stacking of red blood cells in the capillary based on the density of the molecules. The density fraction containing low-density red blood cells, including fetal red blood cells, is recovered and then differentially hemolyzed to preferentially destroy maternal red blood cells. A density gradient in a hypertonic medium is used to separate red blood cells, now enriched in the fetal red blood cells from lymphocytes and ruptured maternal cells. The use of a hypertonic solution shrinks the red blood cells, which increases their density, and facilitates purification from the more dense lymphocytes. After the fetal cells have been isolated, fetal DNA can be purified using standard techniques in the art.

Further, an agent that stabilizes cell membranes may be added to the maternal blood to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenyloin, zinc citrate, mexitil, dilantin, sodium hyaluronate, or polaxamer 188.

An example of a protocol for using this agent is as follows: The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

iii. Plasma-Free Fetal DNA

Genomic DNA may be isolated from the plasma using the Qiagen Midi Kit for purification of DNA from blood cells, following the manufacturer's instructions (QIAmp DNA Blood Midi Kit, Catalog number 51183). DNA is eluted in 100 mu·l of distilled water. The Qiagen Midi Kit also is used to isolate DNA from the maternal cells contained in the "buffy coat."

Finally, it is noted that, in certain embodiments, one may also use samples from tissue, saliva, urine, tear, vaginal secretion, breast fluid, breast milk, or sweat.

B. Distribution of DNA Molecules

In the illustrated method, the genomic DNA obtained from a maternal tissue as described above is diluted into multiple reaction samples, e.g. in multiwell plates, so that there is, on average, less than one genome equivalent per well. Thus, when the individual discrete samples are analyzed for the presence of the genetic abnormality to be tested, the DNA (chromosome) to be analyzed will, on average, either be present or absent, permitting so-called "digital analysis." A reaction sample in general will contain a single template molecule (haplotype), two target molecules (diploid) or three target molecules (trisomy).

The wells provide discrete reaction samples and may be implemented in a number of devices, such as a microtiter plates, beads in an emulsion, or a microfluidic device. These are described in detail below. The device must be capable of carrying out a large number of discrete amplification reactions. As described below, this number should be, at a minimum, 10,000 reactions, and preferably on the order of 100,000 reactions. The reaction sample is preferably holds about 10-100 µL of a PCR reaction sample containing the genomic DNA, nucleotides (dNTPs), polymerase and appropriate PCR primers. The primers are used in conjunction with a label for rapid quantitative detection of PCR products. The type of labeling will depend on the amplification/detection system used, e.g., a "molecular beacon" fluorescent probe for microtiter plate based amplification. This type of probe is described, for example, in Vogelstein et al, supra. Alternatively, labeling may be done with SYBR Green, which has very low fluorescence in the absence of double stranded DNA and very high fluorescence in the presence of double stranded DNA.

Another form of parallel analysis useful in the present invention is single molecule analysis. Again, a sample is diluted to contain less than a nominal single genome equivalent of DNA, and the presence of the target of interest (i.e., chromosome 21 trisomy) can be determined in a large number of samples. By analyzing a large number of samples, the fetal DNA can be distinguished from the maternal DNA. This is termed a "digital analysis," because each well will have, on average, one genome equivalent per cell, and furthermore, the dilution may be read as a binary "yes-no" result as to the presence of the chromosome or other sequence to be counted.

Another method for single molecule analysis involves the use of site-specific fluorescent tags that are detected as the DNA is drawn through a microfluidic device in a single molecule, elongated flow. An example of this technique, described below, is termed "direct linear analysis," or DLA.

C. Detection and Quantification

Having isolated the sample DNA into a nominal genome equivalent, the presence of the DNA sequence or chromosome of interest must be quantified. This may be done either in single molecule mode, or with an amplified product.

While the preferred embodiment of the invention is described in terms of PCR, the invention is primarily directed to the use of multiple individual genetic sequence detections. In some embodiments, the method of amplification maybe, for example, self-sustained sequence reaction, ligase chain reaction, rapid amplification of cDNA ends, polymerase chain reaction and ligase chain reaction, Q-beta phage amplification, strand displacement amplification, or splice overlap extension polymerase chain reaction.

Also, while detection may be conveniently be carried out by a sequence specific probe, detection may also be carried out by directly sequencing a region of interest to determine if it is the target sequence of interest.

1. Digital PCR Methods

While the presently known PCR methods may be multiplexed, that is, run with multiple primers to multiple targets, it is preferred to limit the number of primer pairs in a given reaction. Generally, there will be two primer pairs: one for amplifying a test sequence, and another pair for amplifying a control sequence. Primers are designed according to known parameters for avoiding secondary structures and self-hybridization. Further, both primer pairs should anneal and melt at about the same temperatures.

Primers

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers is incorporated into the products from each loci of interest, thus the TM can be recalculated based on both the sequences of the 5' half and the 3' half of each primer. Any DNA polymerase that catalyzes primer extension can be used including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™. Genomic DNA polymerase, or sequenase. Preferably, a thermostable DNA polymerase is used. A "hot start" PCR can also be performed wherein the reaction is heated to 95° C. for two minutes prior to addition of the polymerase or the polymerase can be kept inactive until the first heating step in cycle 1. "Hot start" PCR can be used to minimize nonspecific amplification. Any number of PCR cycles can be used to amplify the DNA, including but not limited to 2, 5, 10, 15, 20, 25, 30, 35, 40, or 45 cycles. In a most preferred embodiment, the number of PCR cycles performed is such that equimolar amounts of each loci of interest are produced.

A number of specific PCR primers are useful in the present process, such as those disclosed in technical literature of Qiagen. That literature describes a protocol where DNA was purified from peripheral blood and amniocyte cultures using the QIAmp DNA Blood Mini Kit. For amplification of the amyloid gene on chromosome 21, (NCBI gene ID 473931, accession NC_006488) primer and probe sequences were:

SEQ ID NO: 1: forward primer, 5'-GGG AGC TGG TAC AGA AAT GAC TTC-3'; reverse primer, SEQ ID NO: 10: 5'-TTG CTC ATT GCG CTG ACA A-3'; and probe, SEQ ID NO: 2 5'-(FAM) AGC CAT CCT TCC CGG GCC TAG G (TAMRA)-3'.

For amplification of GAPDH, (GenBank locus 12p13.31-p13.1) primers and probe were: forward primer, SEQ ID NO: 3, 5'-CCC CAC ACA CAT GCA CTT ACC-3'; reverse primer, SEQ ID NO: 4, 5'-CCT ACT CCC AGG GCT TTG ATT-3'; and probe, SEQ ID NO: 5, 5'-(VIC) AAA GAG CTA GGA AGG ACA GGC AAC TTG GC (TAMRA)-3'. PCR was performed using the TaqMan system, with 2 µl of template DNA in each 25 µl reaction and final concentrations of 300 nmol/liter of each primer and 150 nmol/liter of each dual-labeled TaqMan probe. Cycling conditions were incubation at 50° C. for 2 minutes, then 95° C. for 10 minutes, followed by 40 cycles of 60° C., 1 minute and 95° C., 15 seconds.

Using the above exemplary protocol, the different ratio of the amyloid gene and the GAPDH gene in karyotypically normal and trisomy 21 samples was clearly distinguishable in the multiplex PCR assay, as reported in the Qiagen product literature. Assays using a dilution series of the DNA template showed that the difference remained clear over a wide range of template concentrations and with starting concentrations of DNA as low as 10 mg/liter. Of course, in a maternal blood sample, the concentration of fetal DNA would be much lower.

Fluorescent in Situ Amplification

Fluorescent probe-based technologies, which can be performed on the PCR products "in situ" (i.e., in the same wells), are particularly well suited for this application. This method is described in detail in Vogelstein PNAS 96:9236, above, and Vogelstein et al. "Digital Amplification," U.S. Pat. No. 6,440,705, hereby incorporated by reference for its description of this amplification procedure.

The "digi-PCR" method of Vogelstein et al. is described in the above-mentioned patent. An exemplary protocol as set forth in that patent is as follows: PCR is performed in 7 µl volumes in 96 well polypropylene PCR plates (Marsh Biomedical Products, Rochester, N.Y.). The composition of the reactions is: 67 mM Tris, pH 8.8, 16.6 mM $NH_4 SO_4$, 6.7 mM $MgCl_2$, 10 mM β-mercaptoethanol, 1 mM dATP, 1 mM dCTP, 1 mM dGTP, 1 mM TTP, 6% DMSO, 1 µM primer F1, 1 µM primer R1, 0.05 units/µl Platinum Taq polymerase (Life Technologies, Inc.), and "one-half genome equivalent" of DNA.

To determine the amount of DNA corresponding to one-half genome equivalent, DNA samples are serially diluted and tested via PCR. The amount that yielded amplification products in half the wells, usually about 1.5 pg of total DNA, is defined as "one-half genome equivalent" and used in each well of subsequent Digital Amplification experiments. Fifty µl light mineral oil (Sigma M-3516) is added to each well and reactions performed in a HybAid Thermal cycler at the following temperatures: denaturation at 94° C. for one min; 60 cycles of 94° C. for 15 sec, 55° C. for 15 sec., 70° C. for 15 seconds; 70° C. for five minutes.

MB, or molecular beacon probes, which become fluorescent on binding to the target sequence(s), as described in more detail below, may be used as follows:

For fluorescence analysis, 3.5 µl of a solution with the following composition is added to each well: 67 mM Tris, pH 8.8, 16.6 mM $NH_4 SO_4$, 6.7 mM $MgCl_2$, 10 mM β-mercaptoethanol, 1 mM dATP, 1 mM dCTP, 1 mM dGTP, 1 mM TTP, 6% DMSO, 5 µM primer, 1 µM MB-GREEN, 1 µM MB-RED, 0.1 units/µl Platinum Taq polymerase. The plates are centrifuged for 20 seconds at 6000 g and fluorescence read at excitation/emission wavelengths of 485 nm/530 nm for MB-GREEN and 530 nm/590 nm for MB-RED. The plates are then placed in a thermal cycler for asymmetric amplification at the following temperatures: 94° C. for one minute; 10-15 cycles of 94° C. for 15 sec, 55° C. for 15 sec., 70° C. for 15 seconds; 94° C. for one minute; and 60° C. for five minutes. The plates are then incubated at room temperature for ten to sixty minutes and fluorescence measured as described above.

MB probes are oligonucleotides with stem-loop structures that contain a fluorescent dye at the 5' end and a quenching agent (Dabcyl) at the 3' end. The degree of quenching via fluorescence energy resonance transfer is inversely proportional to the 6th power of the distance between the Dabcyl group and the fluorescent dye. After heating and cooling, MB probes reform a stem-loop structure, which quenches the fluorescent signal from the dye. If a PCR product whose sequence is complementary to the loop sequence is present during the heating/cooling cycle, hybridization of the MB to one strand of the PCR product will increase the distance between the Dabcyl and the dye, resulting in increased fluorescence.

The examples below use a PCR protocol, which also relies on MB type probes, except in connection with a microfluidic device.

The present digital PCR methods may be used with RNA as well as DNA. Isolation of plasma RNA is described below. In this case, cDNA copies are made and then amplified by DNA polymerase-based PCR. Different primers may be used for cDNA synthesis. Specific templates, based on genetic sequences in the chromosomes of interest are preferred. See, Bustina et al., "Pitfalls of Quantitative Real-Time Reverse-Transcription Polymerase Chain Reaction," Journal of Biomolecular Techniques, 15:155-166 (2004). Use of mRNA from constitutively expressed, i.e., housekeeping genes, may be used for a control, and genes that are highly expressed in placenta (described below) are preferred. Currently four different chemistries, TaqMan® (Applied Biosystems, Foster City, Calif., USA), Molecular Beacons, Scorpions® and SYBR® Green (Molecular Probes), are available for real-time PCR. All of these chemistries allow detection of PCR products via the generation of a fluorescent signal and may be adapted to reverse-transcription PCR. Ambion's MessageSensor™ RT Kit includes an RNase H+MMLV RT. MessageSensor includes a total RNA control, a control human GAPDH primer set, RNase inhibitor, and nucleotides, as well as a buffer additive that enables detection with SYBR® Green dye. Ambion recommends using 18S rRNA as an internal control because it shows less variance in expression across treatment conditions than β-actin and GAPDH. A chromosome 21-encoded gene (LOC90625) which shows strong expression in first trimester placenta similar to CSH1 (human placental lactogen) and was selected for plasma analysis in Oudejans et al., "Detection of Chromosome 21-encoded mRNA of Placental Origin in Maternal Plasma," *Clinical Chemistry* 49: 1445-1449, 2003. Specific primers for use with this gene are given in this paper. Uniquely expressed chromosome 21 transcripts are described at Gardiner et al., "Analysis of human chromosome 21: correlation of physical and cytogenetic maps; gene and CpG island distributions," *E.M.B.O.J.* 9(1):25-34 (1990), namely cDNA of identified products ETS2, MX1, MX2, CBS, COL6A1 and BCEI, which can be partially sequenced or mapped according to the present methods.

2. Bead Emulsion PCR

Emulsion PCR has been used to prepare small beads with clonally amplified DNA—in essence, each bead contains one type of amplicon of digital PCR. (Dressman et al, *Proc. Natl. Acad. Sci. USA*. 100, 8817 (Jul. 22, 2003)). By using specific primers for regions of chromosomes A and B while performing emulsion PCR, one will create beads with digital amplicons from only these two chromosomes, and it is only necessary to count the number of positive beads of each type. There are many ways to do this; we will point out two of them. First, use two different species of beads (either in size or fluorescent labeling) to anchor the two amplicons respectively. Alternatively, one could label the non-anchored primers with different fluorophores and use a single bead type. After amplification, the positive beads (amplicons) of each type can be counted with methods such as flow cytometry or simply by counting them in a suitably equipped microscope.

This technique is further described in Dressman et al (supra) and Dressman et al. PCT publication WO2005010145, "METHOD AND COMPOSITIONS FOR DETECTION AND ENUMERATION OF GENETIC VARIATIONS," published 2005-02-03, and hereby incorporated by reference for its description of a bead-based process. Briefly, in Step 1, Magnetic beads covalently coated with streptavidin are bound to biotinylated oligonucleotides ("oligos"). In Step 2, an aqueous mix containing all the necessary components for PCR plus primer-bound beads and template DNA are stirred together with an oil/detergent mix to create microemulsions. The aqueous compartments (which may be illustrated as small droplets in an oil layer) contain an average of <1 template molecule and <1 bead. Different templates (control and test) may be pictured in one or less droplets to represent two template molecules whose sequences differ by one or many nucleotides. In Step 3, the microemulsions are temperature cycled as in a conventional PCR. If a DNA template and a bead are present together in a single aqueous compartment, the bead bound oligonucleotides act as primers for amplification. Then, one may picture straight lines corresponding to PCR products attached to the corresponding templates connected to the beads to represent extension products from the two different kinds of templates. In Step 4, the emulsions are broken and the beads are purified with a magnet. In Step 5, after denaturation, the beads are incubated with oligonucleotides that can distinguish between the sequences of the different kinds of templates. Fluorescently labeled antibodies are then used to label the bound hybridization probes. This renders the beads containing PCR product as different colors (e.g., red or green) upon appropriate laser excitation. In Step 6, flow cytometry is used to count the red and green beads. Preferably each bead is bound to at least 10, 50, 100, 500, or 1000 molecules of the same nucleic acid sequence.

For purposes of detailed description, the following example is taken from the above-quoted PCT publication: Detailed Exemplary Protocol Using Bead Emulsions Step 1—Coupling oligonucleotides to beads. Superparamagnetic beads of 1.05±0.1 um in diameter, covalently bound to streptavidin, are purchased from Dynal Biotech, Inc. (650.01, Lake Success, N.Y.). Beads are washed once with 1×PCR buffer (53286, Invitrogen, Carlsbad, Calif.) then suspended in Bind and Wash Buffer (BWB) (5 mMTris-HCl, 0.5 mM EDTA, 1.0 MNaCl, pH 7.5). Beads are incubated in BWB for 30 min at room temperature in the presence of 10 μM oligonucleotides. These oligonucleotides are modified with a dual biotin group at the 5'end with the biotin groups separated by a six-carbon linker (IDT, Coralville, Iowa). After binding, the beads are washed 3 times with 1×PCR buffer to thoroughly remove unbound oligonucleotides.

Step 2—Preparing microemulsions. Microemulsions for PCR are prepared in an oil phase that is composed of 4.5% Span 80 (S6760, Sigma, St. Louis, Mo.), 0.40% Tween 80 (Sigma S-8074), and 0.05% Triton X-100 (Sigma T-9284) in mineral oil (Sigma M-3516). The aqueous phase consists of 67 mMTris-HCl (pH 8. 8), 16.6 mM NH4SO4, 6.7 mMMgCl2, 10 mM (3-mercaptoethanol, 1 mMdATP, 1 mMdCTP, 1 mMdGTP, 1 mMdTTP, 0.05 μM forward primer, 25 μM reverse primer, 45 units Platinum Taq(Invitrogen 10966-034), various amounts of template DNA, and ~108 oligonucleotide-coupled beads in a total volume of 300 μl. The forward primer is an oligonucleotide whose sequence is identical to the 3'20-22 nt of that described in step 1 and is not modified with biotin.

Water-in-oil microemulsions are prepared by drop wise addition of 200 microliters of the aqueous phase to 400 microliters of the oil phase previously placed in a 2 ml round bottom cryogenic vial (430661, Corning, Corning, N.Y.).

The drop wise addition is performed over-one minute while the mixture is being stirred at 1400 RPM with a magnetic microstir bar (58948-353, VWR, Plainfield, N.J.) on a VWR model 565 Magnetic Stirrer. After the addition of the aqueous phase, the mixture continued to be stirred for a total time of 30 minutes. Two emulsions are made at once by placing two tubes in a rack placed at the center of the magnetic stirrer.

Step 3—PCR cycling. The emulsions are aliquoted into five wells of a 96 well PCR plate, each containing 100 µl. PCR is carried out under the following cycling conditions: 94° C. for 2 minutes; 40 cycles of 94° C. for 15 seconds, 57° C. for 30 seconds, 70° C. for 30 seconds. The PCR products analyzed in this study ranged from 189 to 239 bp.

Step 4—Magnetic capture of beads. After PCR cycling, the microemulsion from five wells of a PCR plate are pooled and broken by the addition 800 microliters of NX buffer (100 mMNaCl containing 1% Triton X-100, 10 mMTris-HCl, pH 7.5, 1 mM EDTA) in a 1.5 ml tube (Corning 430909). After vortexing for-20 sec. the beads are pelleted by centrifugation in a microcentrifuge at 8000 rpm (5000 g) for 90 seconds. The top oil phase, and all but-300 microliters of the aqueous phase, is removed from the tube and 600 microliters of NX buffer is added. These steps are repeated. The tube is then placed on a magnet (Dynal MPC-S) and the rest of the supernatant is carefully pipetted off. The beads are washed an additional 3 times with 1×PCR buffer using magnetic separation rather than centrifugation and finally re-suspended in 100 microliters of 1×PCR buffer.

Step 5—Sequence differentiation. Two oligonucleotide probes are used for each reaction. One is 5'-labeled with 6-carboxyfluorescein (6-FAM) and is specific for one allele while the second is 5'-labeled with biotin and is specific for the other allele. Probes are synthesized by IDT. The 30 microliters hybridization reactions contained 10 µM of each probe and 5-25 million beads in 1×PCR buffer. Reactions are performed in PCR plates on a thermal cycler by heating to 94° C. for 30 seconds then cooling to 75° C. at a rate of 0.5° C. per second, cooling to 45° C. at 0.2° C. per second, and finally cooled to 30° C. at 1° C. per second.

All subsequent steps are performed at room temperature. The reactions are transferred to a 96 well Costar plate (Corning 3797) and placed on a 96 well magnet. Beads are collected magnetically by exposing them to the magnet for 2 minutes. The supernatant is removed and the beads washed 3 times with 1×PCR buffer by pipetting them and collecting for two minutes. They are finally resuspended in 100 microliters B-PCR buffer (1 mg/mL BSA in 1×PCR buffer).

The beads are then incubated for 10 minutes in a total volume of 100 microliters B-PCR buffer containing 3 µg of Alexa-488 rabbit anti-fluorescein antibody (Molecular ProbesA-11090, Eugene, Oreg.) and 3 µg of Nutravidin labeled with R-phycoerytbrin (Molecular Probes A-2660) in B-PCR buffer. The beads are washed three times and resuspended in B-PCR buffer as described above. They are then incubated for ten minutes in a total volume of 100 microliters B-PCR buffer containing 6 µg of Alexa 488-conjugated chicken anti-rabbit antibody (Molecular Probes A-21441) and 3 µg of biotinylated goat anti-avidin antibody (BA-0300, Vector Laboratories, Burlingame, Calif.). The beads are washed three times and resuspended in B-PCR buffer as described above. They are then incubated for ten minutes in a total volume of 100 microliters B-PCR buffer containing 3 µg of an Alexa 488-conjugated goat anti-chicken antibody (Molecular Probes A-11039) and 3 micrograms of R-phycoerytbrin-labeled streptavidin (Molecular Probes S-866). This solution is then washed an additional 3 times with 1×PCR buffer and resuspended in 20 microliters of 1×PCR buffer.

Step 6—Flow Cytometry. The bead suspension is diluted to a concentration of—106-107 beads per ml in 10 mMTris-HCl, 1 mMEDTA (351-010-131, Quality Biological, Inc., Gaithersburg, Md.) and analyzed using a LSR instrument (BD Biosciences, Franklin Lakes, N.J.). The instrument is set up for standard two-color analysis using an argon laser and optical filters that distinguished between the two fluorescent dyes. No spectral deconvolution is required as the major bead populations are well separated. In some cases, scanning is performed with FACScan or FACSCalibur instruments (BD Biosciences).

3. Microfluidic Dilution with PCR

Another approach to digital PCR involves the use of microfluidics to achieve the digital PCR conditions used in the present method.

Generally, a DNA sample obtained as described above is diluted into an appropriate concentration, mixed with PCR reagents, primers, dNTPs, etc. and flowed through a number of channels which may be closed off in multiple segments, resulting in a number of discrete reaction samples, or chambers. The chambers may be subjected to PCR thermal cycling and the products quantitatively detected by florescence, as described above.

A suitable microfluidic device is produced by Fluidigm Corporation, termed the Digital Isolation and Detection IFC (integrated fluid circuit). A suitable device is also described in U.S. Pat. No. 6,960,437 to Enzelberger, et al., issued Nov. 1, 2005 entitled "Nucleic acid amplification utilizing microfluidic devices," hereby incorporated by reference for purposes of describing a microfluidic device capable of supporting multiple parallel nucleic acid amplifications and detections. As described in this patent, one exemplary microfluidic device for conducting thermal cycling reactions includes in the layer with the flow channels a plurality of sample inputs, a mixing T-junction, a central circulation loop (i.e., the substantially circular flow channel), and an output channel. The intersection of a control channel with a flow channel can form a microvalve. This is so because the control and flow channels are separated by a thin elastomeric membrane that can be deflected into the flow channel or retracted therefrom. Deflection or retraction of the elastomeric membrane is achieved by generating a force that causes the deflection or retraction to occur. In certain systems, this is accomplished by increasing or decreasing pressure in the control channel as compared to the flow channel with which the control channel intersects. However, a wide variety of other approaches can be utilized to actuate the valves including various electrostatic, magnetic, electrolytic and electrokinetic approaches. Another microfluidic device, adapted to perform PCR reactions, and useful in the present methods, is described in US 2005/0252773 by McBride, et al., published Nov. 17, 2005, entitled "Thermal reaction device and method for using the same."

The substantially circular central loop and the control channels that intersect with it form the central part of the rotary pump. The pump(s) that cause solution to be flowed through the substantially circular flow channel consist of a set of at least three control channels that are adjacent to one another and which intersect the substantially circular branch flow channel (i.e., the central loop). When a series of on/off actuation sequences are applied to the control channels, the fluid in the central loop can be peristaltically pumped in a chosen direction, either clockwise or counterclockwise. The peristaltic pumping action results from the sequential deflection of the membranes separating the control channels and flow channel into or out of the flow channel. In general, the higher the actuation frequency, the faster the fluid rotates through the central loop. However, a point of saturation is eventually reached at which increased frequency does not result in faster fluid flow. This is primarily due to limitations in the rate at which the membrane can return to an unactuated position. One system exemplified has two sets of pumps and (i.e., two sets of three control channels that overlay the substantially circular flow channel) a single pump can be utilized (i.e., a single set of three control channels overlaying the substantially circular flow channel). Furthermore, while each pump is shown as including three control channels, more control channels can be utilized. It should also be understood that the three control channels can be different segments of a single control channel that overlay the flow channel.

The detailed description of multiple sample analysis being carried out in wells does not mean that the target sequences need to be physically separated into wells, as the sequences may be in samples which are isolated simply by being on different beads (as described above) or by adherence to different areas of a substrate (as described below).

4. Single Molecule Detection/Sequencing Methods

It should be appreciated that methods involving PCR or other amplification are not the only way to detect or enumerate the molecules in a given discrete reaction sample. It is possible to use single molecule flow cytometry to count single molecules that have been labeled with a sequence-specific fluorescent probe. It is also possible to sequence the target sequence in the reaction sample directly, either after amplification or at the single molecule level.

Fluorescent Nucleotide Incorporation by DNA Polymerase

As described in the above-referenced PNAS publication by Braslaysky et al., DNA polymerase may be employed to image sequence information in a single DNA template as its complementary strand is synthesized. The nucleotides are inserted sequentially; only the time resolution to discriminate successive incorporations is required. After each successful incorporation event, a fluorescent signal is measured and then nulled by photobleaching. This method lends itself to massive parallelism.

Briefly, this technique permits observations of single molecule fluorescence by a conventional microscope equipped with total internal reflection illumination, which reduces background fluorescence. The surface of a quartz slide is chemically treated to specifically anchor DNA templates while preventing nonspecific binding of free nucleotides, and a plastic flow cell is attached to the surface to exchange solutions. DNA template oligonucleotides are hybridized to a fluorescently labeled primer and bound to the surface via streptavidin and biotin with a surface density low enough to resolve single molecules. The primed templates are detected through their fluorescent tags, their locations are recorded for future reference, and the tags are photobleached. Labeled nucleotide triphosphates and DNA polymerase enzyme are then washed in and out of the flow cell while the known locations of the DNA templates are monitored for the appearance of fluorescence. The technique uses a combination of evanescent wave microscopy and single-pair fluorescence resonance energy transfer (spFRET) to reject unwanted noise. The donor fluorophore excites acceptors only within the Forster radius, thus effectively creating an extremely high-resolution near-field source. Because the Forster radius of this fluorophore pair is 5 nm, the spatial resolution of this method exceeds the diffraction limit by a factor of 50 and conventional near-field microscopy by an order of magnitude.

The genomic DNA from the tissue taken from the mother, i.e. the mixture of fetal and maternal genetic material, may be distributed into discrete samples which are anchored to a surface and sequenced or monitored by labeled probes to detect a target specific sequence, e.g., a unique region of chromosome 21, e.g., AML1. Further guidance for the preparation of chromosome 21-unique sequences may be found, for example, in Fuscoe et al., "An Efficient Method for Selecting Unique-Sequence Clones from DNA Libraries and Its Application To Fluorescent Staining of Human Chromosome 21 Using in Situ Hybridization," *Genomics*, vol. 5, 1989, pp. 100-109. A methodology useful in the present invention platform is based on massively parallel sequencing of millions of fragments using attachment of randomly fragmented genomic DNA to a planar, optically transparent surface and solid phase amplification to create a high density sequencing flow cell with millions of clusters, each containing ~1,000 copies of template per sq. cm. These templates are sequenced using four-color DNA sequencing-by-synthesis technology. See, products offered by Illumina, Inc., San Diego Calif. Also, see US 2003/0022207 to Balasubramanian, et al., published Jan. 30, 2003, entitled "Arrayed polynucleotides and their use in genome analysis."

Sequencing may be combined with amplification-based methods in a microfluidic chip having reaction chambers for both PCR and microscopic template-based sequencing. Only about 30 bp of random sequence information are needed to identify a sequence as belonging to a specific human chromosome. Longer sequences can uniquely identify more particular targets. An algorithm for designing unique sequences is described in Yamada, et al. "PrimerStation: a highly specific multiplex genomic PCR primer design server for the human genome," *Nucleic Acids Res.*, Jul. 1, 2006; 34(Web Server issue): W665-W669, illustrative of software methods that can be used to identify a sequence in comparison to the known genome sequence. See, also Zhu et al., "Single molecule profiling of alternative pre-mRNA splicing," *Science*. 2003 Aug. 8; 301(5634):836-838, describing a single-molecule-based technology for studying mRNA.

Direct Linear Analysis (DLA)

Another method of determining the identity of genomic DNA from the present samples is termed direct linear analysis, and is described in Chan et al. "DNA Mapping Using Microfluidic Stretching and Single-Molecule Detection of Fluorescent Site-Specific Tags," *Genome Research* 14:1137-1146 (2004). In this method, a microfluidic device is used for stretching DNA molecules in elongational flow that is coupled to a multicolor detection system capable of single-fluorophore sensitivity. Double-stranded DNA molecules are tagged at sequence-specific motif sites with fluorescent bisPNA (Peptide Nucleic Acid) tags. The DNA molecules are then stretched in the microfluidic device and driven in a flow stream past confocal fluorescence detectors. DLA can provide the spatial locations of multiple specific sequence motifs along individual DNA molecules, and thousands of individual molecules can be analyzed per minute.

A microchip configuration and operating conditions may be prepared according to this publication that are adequate for stretching 50-kb long DNA. The chip includes a post field, a funnel with a 10:1 taper reduction ratio, a taper shape providing $W(x)1/x2$ profile (W is the channel width, and x is the coordinate along the flow direction), and a 5 μm-wide interrogation channel. The interrogation channel has uniform cross-section to ensure constant solution velocity, which was 10-15 µm/msec. Once inside the channel, stretched and tagged DNA molecules travel through spots of focused laser light that excites fluorescence. Epi-illumination of the sample and confocal detection are arranged within a fluorescence microscope.

The excitation laser beams are directed into the microscope objective with a dichroic mirror that reflects the light with 532 nm (beam ExI) and 633 nm (beams ExII and ExIII) wavelengths, but is transparent to the fluorescence emission excited by these beams. The emission is further split by another dichroic mirror and bandpass filters. Fluorescence excited by the green laser is delivered by optical fiber to the photon-counting avalanche photodiode (APD) for signal detection in data channel 1. Fluorescence excited by red beams ExII and ExIII is directed to the APDs of data channels 2 and 3, respectively.

The above-described device may be configured with larger path lengths in order to accommodate larger DNA strands, presumably up to entire chromosome lengths. The genomic sample is probed with a chromosome 21 specific probe threaded through the interrogation channel, and the presence of one or more chromosomes is detected.

D. Quantitative Evaluation

Digital PCR allows the detection of aneuploidy merely by counting transcripts, as illustrated by the following calculation. Suppose that fetal DNA is present in maternal blood at a fraction level of $\epsilon$, and that we are trying to discover an aneuploidy of order $\alpha$ relative to euploidy e (in the example relating to detection of Down Syndrome in humans, e=2 is euploidy and the Down Syndrome trisomy $\alpha$=3). If chromosome A is euploid and represents an internal control, and chromosome B is aneuploid and is the target to be measured, then one can amplify representative segments from both chromosomes via digital PCR. In comparing the amplicons of each type, one expects to find that for every e amplicons from chromosome A there are $e(1-\epsilon)+\alpha\epsilon$ amplicons from chromosome B. In the case of a trisomy and $\epsilon$=3%, then for every 2 amplicons from chromosome A one expects 2.03 amplicons from chromosome B. While this difference is small, it can be measured. For example, if one amplifies a sample from 1,000 cell equivalents, then one expects 2,000 amplicons from chromosome A and 2,030 from chromosome B. The difference of 30 amplicons is in principle detectable.

The requisite statistical confidence to resolve the difference in proportions can be estimated as follows. There is a random statistical variation associated with the initial sample size, which goes roughly as the square root of the number of samples taken. It is in fact often difficult to precisely start with a fixed number of cell equivalents, and in the previous example we expect statistical error of order 32 amplicons (32~square root(1,000)) for most sample preparation techniques. This is the same size as the signal we are trying to detect and thus in practice one requires more than 1,000 cell equivalents for robust detection. Precisely how many one requires depends on the statistical certainty that is required. If one would like a result that is significant to k standard deviations, then $$k\sqrt{N}=N(e(1-\epsilon)+\alpha\epsilon-e)=N\epsilon(\alpha-e)$$

or $N=(k/(\epsilon(\alpha-e)))^2$

Using the values of the previous example, if we require k=3 standard deviations, then the number of amplicons N must be at least 10,000 for Down Syndrome detection. However, as discussed above, the number of target sequences needed for statistical confidence may be reduced by using controls sequences, and, in addition, the sample may be enriched for fetal DNA.

III. Specific Applications

The present invention is particularly adapted to detecting genetic abnormalities that involve quantitative differences between maternal and fetal genetic sequences. These genetic abnormalities include mutations that may be heterozygous and homozygous between maternal and fetal DNA, and to aneuploidies. For example, a missing copy of chromosome X (monosomy X) results in Turner's Syndrome, while an additional copy of chromosome 21 results in Down Syndrome. Other diseases such as Edward's Syndrome and Patau Syndrome are caused by an additional copy of chromosome 18, and chromosome 13, respectively. The present method may be used for detection of a translocation, addition, amplification, transversion, inversion, aneuploidy, polyploidy, monosomy, trisomy, trisomy 21, trisomy 13, trisomy 14, trisomy 15, trisomy 16, trisomy 18, trisomy 22, triploidy, tetraploidy, and sex chromosome abnormalities including but not limited to XO, XXY, XYY, and XXX.

Other chromosome specific primers are disclosed in United States Patent Application 20050164241 to Hahn, Sinuhe, et al., published Jul. 28, 2005, entitled "Non-invasive detection of fetal genetic traits," hereby incorporated by reference in its entirety for describing methods of sample preparation and certain PCR primers, described as follows:

The primers for the genes are prepared on the basis of nucleotide sequences obtained from databases such as GenBank, EMBL and the like. The names of the polymorphic primers and the sequences of the primers for the genes will be shown for the respective chromosomes in the following examples (#2, Example 1; #4, Example 6, #14, Example 9; #22, Example 2). The following genetic markers and polymorphic makers (Polymorphic STS Primer Pairs: D2S207, D2S177, D2S156 and D2S159, BIOS Laboratories, Inc.) are used to identify chromosome #2.

There are more than 1,000 chromosome 21 specific PCR primer sets listed at the NIH UniSTS web site, which can be located at www(dot)ncbi.nlm.nih.gov/entrez/query.fcgi?db=unists and found with the search phrase "human[organism] AND 21[chr]". UniSTS is a comprehensive database of sequence tagged sites (STSs) derived from STS-based maps and other experiments. STSs are defined by PCR primer pairs and are associated with additional information such as genomic position, genes, and sequences. Similarly, primer sequences for other human chromosomes can be found by appropriately modifying the search query.

Examples of diseases where the target sequence may exist in one copy in the maternal DNA (heterozygous) but cause disease in a fetus (homozygous), include sickle cell anemia, cystic fibrosis, hemophilia, and Tay Sachs disease. Accordingly, using the methods described here, one may distinguish genomes with one mutation from genomes with two mutations.

Sickle-cell anemia is an autosomal recessive disease. Nine-percent of US blacks are heterozygous, while 0.2% are homozygous recessive. The recessive allele causes a single amino acid substitution in the beta chains of hemoglobin.

Tay-Sachs Disease is an autosomal recessive resulting in degeneration of the nervous system. Symptoms manifest after birth. Children homozygous recessive for this allele rarely survive past five years of age. Sufferers lack the ability to make the enzyme N-acetyl-hexosaminidase, which breaks down the GM2 ganglioside lipid.

Another example is phenylketonuria (PKU), a recessively inherited disorder whose sufferers lack the ability to synthesize an enzyme to convert the amino acid phenylalanine into tyrosine Individuals homozygous recessive for this allele have a buildup of phenylalanine and abnormal breakdown products in the urine and blood.

Hemophilia is a group of diseases in which blood does not clot normally. Factors in blood are involved in clotting. Hemophiliacs lacking the normal Factor VIII are said to have Hemophilia A, and those who lack Factor IX have hemophilia B. These genes are carried on the X chromosome, so primers and probes may be used in the present method to detect whether or not a fetus inherited the mother's defective X chromosome, or the father's normal allele.

A listing of gene mutations for which the present method may be adapted is found at www(dot)gdb.org/gdb, The GDB Human Genome Database, The Official World-Wide Database for the Annotation of the Human Genome Hosted by RTI International, North Carolina USA.

A. Preparation for Trisomy with Frequency Analysis

In this protocol, the number of positive reaction samples is used, disregarding increased intensity from three versus two chromosomes in a reaction sample. That is, as described above, trisomy can be detected either by looking for an increased signal from a single well having multiple chromosomal DNA copies, or by diluting a sample and counting the frequency of responses of the trisomic marker versus a control diploid marker.

Fetal DNA circulating in maternal plasma is here used to provide sufficient material for chromosomal analysis. DNA is extracted from a blood sample and aliquoted to different reaction chambers on the basis of genome equivalents, i.e., the entire genomic content of a single normal cell (46 chromosomes). This weighs about 6.6 pg. The term "nominal genome equivalent" is used to refer to the calculated distribution of sample DNA based on a calculated genome size and DNA weight. In practice, there will be some experimental variation in DNA sample size, and, due to random fragment distribution, a given genome equivalent will not contain exactly the DNA fragments corresponding only to a single complete diploid genome, but a large number, on average, will.

For each panel on the Digital Array chip, 10 ul of reaction mix is required. To achieve ~⅓ panel filled, the required final concentration of template in reaction mix should be approximately 48 copies/µl (every 0.33 template per 7 nl chamber). Thus for a 10 µl reaction volume (1 panel), 480 copies (~240 genome equivalents, "GE") of total free-floating DNA is required. These calculations are based on Chiu et al., "Effects of Blood-Processing Protocols on Fetal and Total DNA Quantification in Maternal Plasma," *Clinical Chemistry*, 47:9. 1607-1613. 2001, where real time quantitative PCR was used to estimate plasma DNA isolated under different protocols, and Li Y, Zimmermann et al., "Size Separation of Circulatory DNA in Maternal Plasma Permits Ready Detection of Fetal DNA Polymorphisms," *Clinical Chemistry*, 50:6. 1002-1011. 2004.

Assuming 55% blood volume is plasma, one may obtain 80% recovery from gel extraction with a DNA preparation such as with a QIAEX II kit. If there is 20 ml of blood collected, the volume of plasma=20 ml blood*0.55=11 ml. The total free-floating DNA=11 ml*1000 GE/ml=11000 GE. Therefore, one may calculate the amount of DNA<300 bp, in that 11000 GE*0.27=2970 GE. The amount of DNA<300 bp after recovery=2970 GE*0.8=2376 GE=4752 copies.

Thus, a 20 ml blood draw should contain enough total DNA less than 300 bp (which is about 85% fetal DNA) for about 10 panels, enough, as shown below, to achieve statistical significance.

B. Sample Protocol

The following sample protocol provides a procedure for use in preparing a sample from maternal plasma and increasing the signal from chromosome 21.

Plasma Collection: collect 20 ml peripheral blood from the pregnant subject. This is collected in 2 tubes with EDTA as anticoagulant. Process blood within 2 hours of sample collection. The blood is processed first by centrifugation at 1600 g for 10 min. One aliquots plasma to polypropylene tubes (1 ml each), with care not to disturb buffy coat layer. Next, the supernatant is microcentrifuged at 16000 g (full speed) for 10 min to remove residual maternal cells. Then, one extracts DNA from plasma with QIAamp Blood Mini Kit ("body fluid protocol"). 800 µl of plasma is applied per column and eluted in 40 µl buffer.

Depending on actual DNA concentration in plasma, one may need to process all plasma in a single column (with Midi or Maxi kit) to achieve a higher final concentration of DNA. Then, the DNA is subjected to gel electrophoresis (Li et al Clin. Chem. 50:6 1002-1011 2004) to separate smaller sized DNA fragments. A UV gel tray is prepared with 1% agarose gel with 0.5 mg/L ethidium bromide. 100 bp ladder and HindIII digested Lambda phage DNA is used as markers. The extracted DNA is loaded on a gel; the gel is run at 80V for 1 hour. The DNA is extracted from the gel by first excising DNA<300 bp with clean razor blade. This band is recovered with QIAEX II Gel Extraction Kit (Qiagen) and eluted 40 ul in elution buffer.

Total DNA Quantitation with Real Time PCR:

The amount of total free-floating DNA can be quantified using primers and Taqman probe designed for GAPDH gene (Chromosome 12). Real time PCR is run with GAPDH and Amyloid (Chromosome 21) primers and probes before running with Digital Array to confirm that the amplification regions are intact. To increase the signal from Chromosome 21, an additional set of primers and probes can be used.

One possible candidate is the following (See Blood 104 (1):149-158 (2004):

DSCR1 (Downs Syndrome Critical Region 1) Chr 21

SEQ ID NO: 6:
5' (probe)-AGG TTG TGA AAA CAG CAG CAA TGC AAT GT-(quencher)

P3'
Forward: (SEQ ID NO: 7)
5' CCA CAG GAA GCC GCC TAG T 3'

Reverse (SEQ ID NO: 8):
5' TGA GGG AAG AAA GGA AAC GCT 3'

Amplification region (with primers underlined) SEQ ID NO: 9):
CCACAGGAAGCCGCCTAGTGCAGAGAGGTTGTGA-AAACAGCAGCAATGCAATGTGG AAATTGT AGCGTTTCCTTTCTTCCCTCA. An additional set of primers and probes can be designed to increase signal from the control (these primers can be for chromosome 12 or any other chromosomes except Chromosome 21).

If an automated microfluidic device is used, appropriate channels and valves are provided for introduction of PCR reactants and, if used, a probe.

Figure 2:
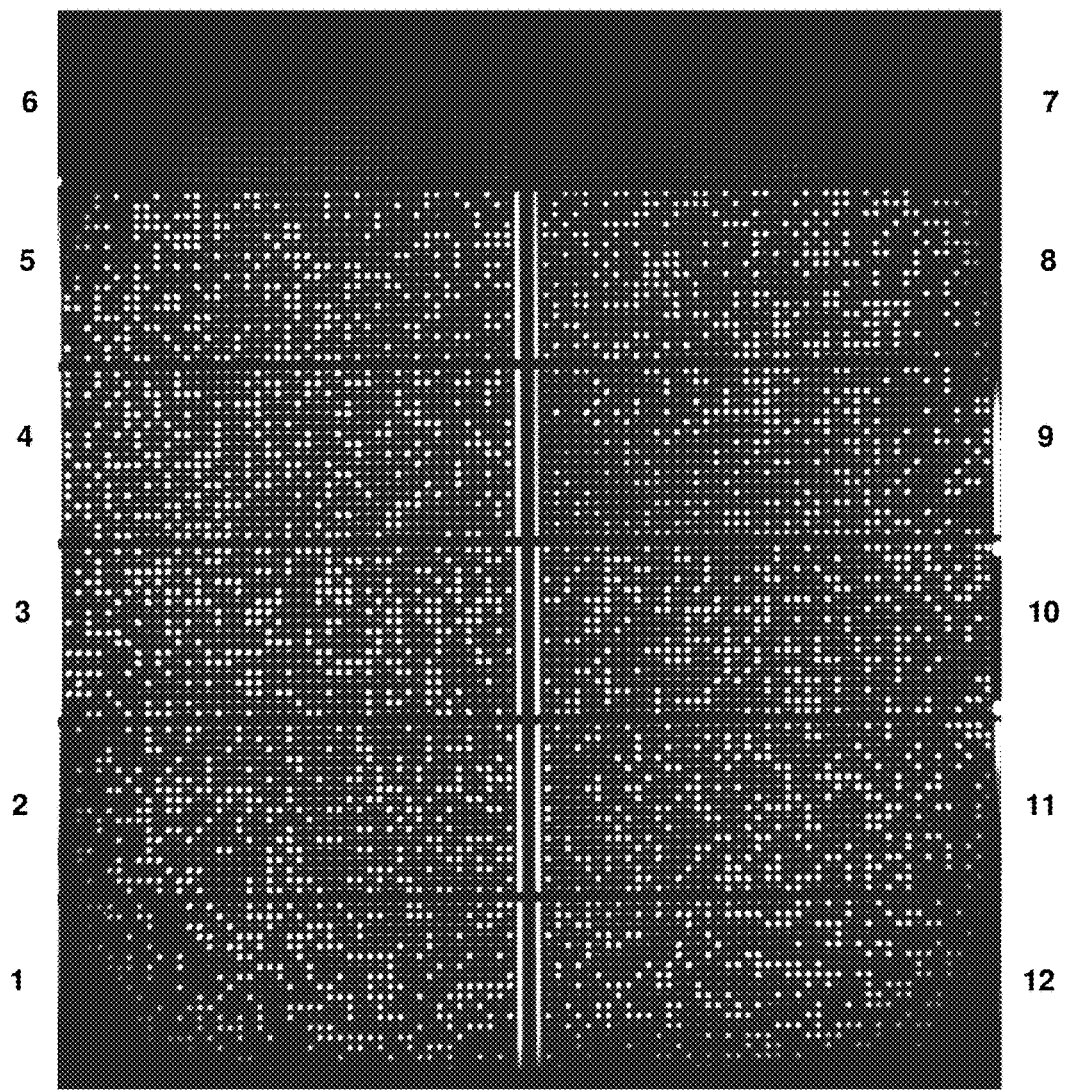
FIG. 2 is a photograph of a microfluidic chip having 12 panels (numbered 1-12) containing DNA with chromosome 21 labeled.
Figure 3:
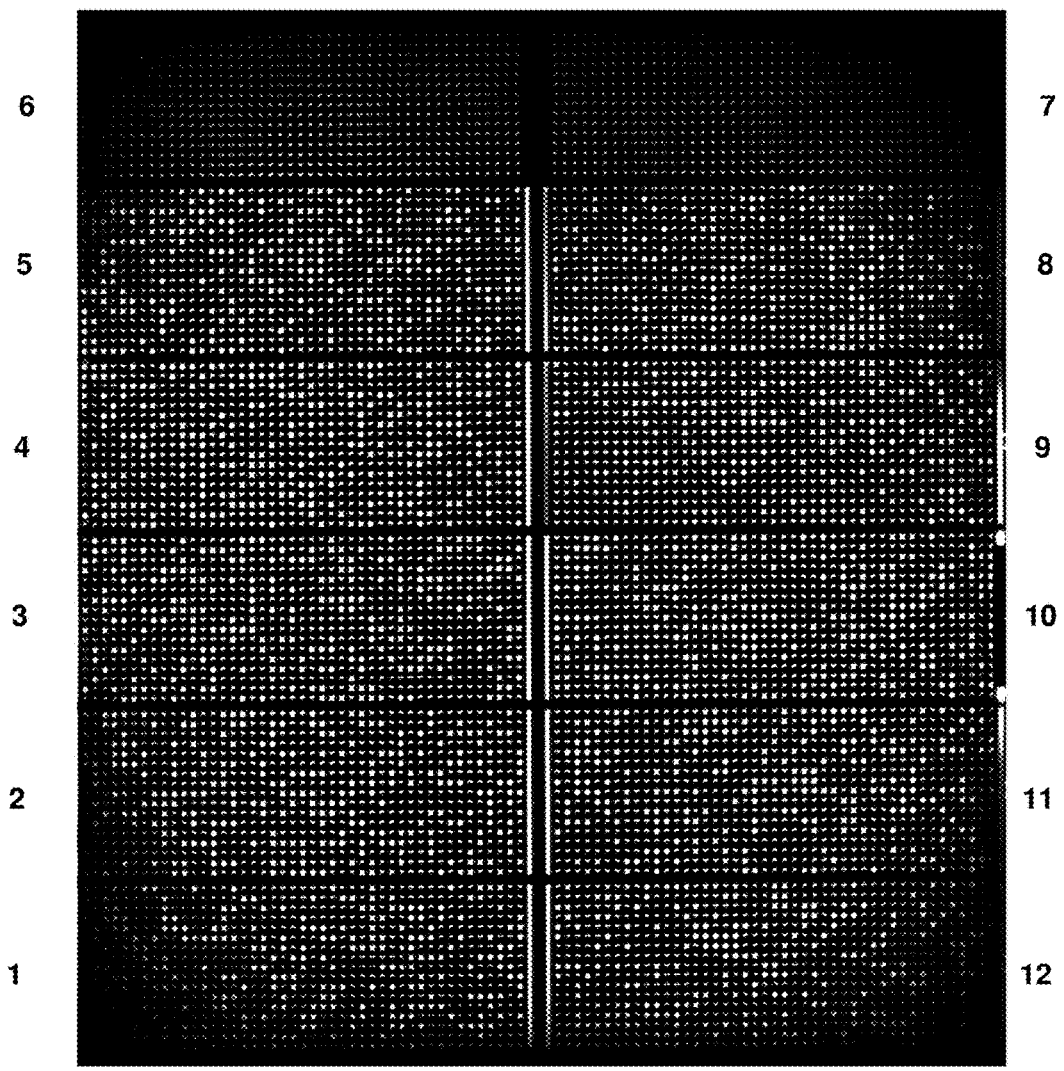
FIG. 3 is a photograph of a microfluidic chip having 12 panels (numbered 1-12) containing DNA with chromosome 12 labeled.

In the Examples below, a Fluidigm prototype DID chip was used. The Digital Isolation and Detection (DID) chip works by partitioning a sample/assay (TaqMan® assays) mixture into hundreds to tens of thousands of reaction chambers, where real-time QPCR reactions are continuously monitored by a dynamic array reader. The DID chip described here contains inputs for 12 sample/assay mixtures, and its architecture partitions 7.5 μL of fluid for each input into 1,200 reaction chambers. These are shown as 12 panels in FIGS. 2 and 3. Instrumentation is used to drive the sample/assay mixtures from the wells in the carrier into the appropriate reaction chambers. As shown in FIGS. 2 and 3, white spots indicate the location of reaction chambers positive for the indicated primer and dye. The sum of the positive wells in each section will be consistent with the gene/chromosome copies that were measured in the sample. The number of light spots shown represents the number of positive reaction chambers; no quantification was used in these experiments, and the results do not depend on quantization of a signal from an individual (discrete) sample mixture. Such quantization can be used, but can also be a source of error in methods that depend on this.

This chip is further described in Ottesen et al., "Microfluidic Digital PCR Enables Multigene Analysis of Individual Environmental Bacteria," *Science* 314:1464-1467 (Dec. 1 2006). As discussed there, the DNA sample is suspended in a PCR reaction buffer and loaded into the microfluidic device. The present work was done a more recent version of that microfluidic device. This device is further described below. As an alternative to the above protocol, one may use a kit with pre-optimized reagents, such as the Qiagen QuantiTect Multiplex PCR Kit, which contains QuantiTect Multiplex PCR Buffer, having synthetic factor MP and an optimized combination of KCl and $(NH_4)_2SO_4$, which promote specific and stable annealing of primers to templates. This kit also contains HotStarTaq DNA Polymerase: Since this polymerase requires incubation at 95° C. for activation, misprimed products and primer-dimers, which can compete for reactants, are not formed during reaction setup.

One also uses the following anti-contamination procedures:
1. Use aerosol resistant pipette tips
2. Preamplification treatment by use of uracil N-glycosylase, which destroyed uracil-containing PCR products/RNA
3. Negative water blank
4. Negative blank gel slices
5. Negative control panel on Digital Array After extraction from blood and purification, the preferred concentration of DNA sample should be ~140-240 copies/μl, i.e., ~70-120 GE/μl. This corresponds to ~3.4 to 2 μl of required template volume in a digital PCR reaction volume of 10 μl.

In this protocol and the following examples, the mixture of maternal and fetal genetic material obtained from the mother is diluted to achieve a high likelihood that only one target sequence will be present in a given sample to be analyzed. As shown in FIG. 1A, it is also possible to carry out this process with less dilution and less empty sample sites if quantitation is used to distinguish a number of target sequences in a sample.

IV. Examples

Presented below are data obtained from genomic DNA extracted from a normal human cell line and from a Down Syndrome cell line (trisomy 21). These cell lines were purchased from ATCC. Taqman PCR primers specific for chromosome 21 and chromosome 12 were adapted from a reference: Zimmermann B et al, "Novel Real-Time Quantitative PCR Test for Trisomy 21". Clinical Chemistry. 48 (no. 2). 2002. 362-363. HEX (hexachloro-6-carboxyfluorescein) and FAM (6-carboxy-fluorescein) are well known fluorescent dyes; BHQ® quencher is black hole quencher dye (BHQ, Biosearch Technologies, Novato, Calif.).

```
Amyloid Forward:
                                        (SEQ ID NO: 11)
5' GGG AGC TGG TAC AGA AAT GAC TTC 3'

Amyloid Reverse:
                                        (SEQ ID NO: 12)
5' TTG CTC ATT GCG CTG ACA A 3'

Amyloid Probe:
                                        (SEQ ID NO: 13)
5' (FAM) AGC CAT CCT TCC CGG GCC TAG G (BHQ)3'

GAPDH Forward:
                                        (SEQ ID NO: 14)
5' CCC CAC ACA CAT GCA CTT ACC 3'

GAPDH Reverse:
                                        (SEQ ID NO: 15)
5' CCT AGT CCC AGG GCT TTG ATT 3'

GAPDH Probe:
                                        (SEQ ID NO: 16)
5' (HEX)AAA GAG CTA GGA AGG ACA GGC AAC TTG GC
(BHQ)3'
primers and probes were synthesized by IDT
(Integrated DNA Technologies)).
```

DNA samples were analyzed by digital PCR using microfluidic Digital PCR on a Fluidigm® microfluidic chip having 12 panels with 765 (wells) partitions each. Various mixtures of normal and Downs DNA (representing a mixture of fetal and maternal cells in a blood sample) were analyzed. Small amounts of each template were pipetted directly into each PCR mix; alternatively, a mixture of templates could be prepared first, then pipetted into the PCR mix, which should yield more accurate results. The alternate method was used in these experiments. In these examples, trisomy is detected based on the number of wells showing the triplicate chromosomal marker, i.e., the analysis illustrated in FIG. 1C. Intensity data of the triplicate chromosome are not used, except as a ratio to a normal chromosome marker. Because the sample is dilute many of the wells will have no chromosome of interest (or marker fragment), as can be seen in FIGS. 2 and 3, which show photographs of chips from Example 2.

Protocol: combine Primers 300 nM; Probes 150 nM; iTaq supermix with ROX or iQ supermix. Tween20 (0.1%); DNA template (2 μl, premixed with the desired percentage of Downs DNA); Water (make up to total reaction volume of 10 μl).

Each panel was loaded with reaction mix of 10 μl, and PCR was performed on a thermal cycler similar to the commercially available BIOMARK System from Fluidigm according to manufacturer's instructions. Cycling conditions were: 98° C. 30 s, 97° C. 30 s, 95° C. 2 min, [56° C. 30 s, 58° C. 30 s, 60° C. 30 s, 98° C. 15 s]×40 cycles, 60° C. for 10 min.

A MATLAB program was written to subtract the image of the chip taken before cycling from that taken at cycle 40 for each fluorescent channel. The number of positive wells in each fluorescent channel was counted.

Figure 4:
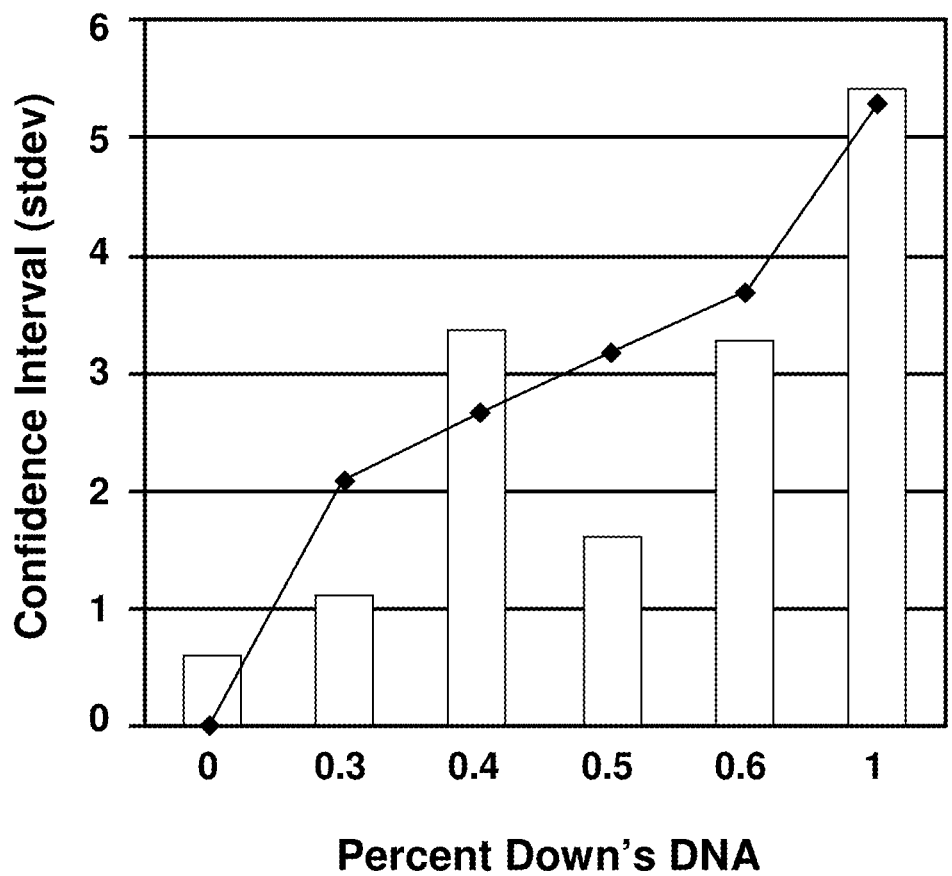
FIG. 4 is a graph showing results from experiments done using digital analysis of mixed normal and trisomic (Down Syndrome, trisomy 21) DNA.

Experiments were done with samples that contained 100% Downs, 60% Downs, 50% Downs, 40% Downs, 30% Downs, and 0% Downs (i.e., 100% Normal) DNA. The results from these experiments are shown in FIG. 4, where each bar and data point represents a different concentration of Down's DNA.

The data from the Data were analyzed as follows:
X*=number of HEX counts (Chromosome 12)
Y*=number of FAM counts (Chromosome 21)

There is a characteristic response for digital PCR. At low copy number, as described further in Warren L, Bryder D, Weissman I R, Quake S R. Transcription factor profiling in individual hematopoietic progenitors by digital RT-PCR. See, PNAS 2006. 103: 17807-17812.).
X=actual input copy number of Chromosome 12
Y=actual input copy number of Chromosome 21

$X=\log(1-X*/N)/\log(1-1/N)$ $Y=\log(1-Y*/N)/\log(1-1/N)$

N=total number of partition per panel=765

Confidence interval $k=(Y-X)/\sqrt{Y}$

In FIG. 4, the confidence level obtained for a single chip was plotted against percent downs DNA and compared to the predicted confidence interval (line). The observed confidence interval at, for example 30% DNA, was less than predicted, but none the less showed a confidence interval of >1 for only one panel.

This calculation was done as follows:
For 1 genomic equivalence,

Copy number of Chromosome $12=2(1-\epsilon)+2\epsilon=2$

Copy number of Chromosome $21=2(1-\epsilon)+3\epsilon=2+\epsilon$

Difference between copy numbers of Chr21 and Chr12=$\epsilon$

Where $\epsilon$=fetal DNA/total free floating DNA*100%

For m genomic equivalence
Y=copy number of Chromosome 21
X=copy number of Chromosome 12
Difference between copy numbers of Chr21 and Chr12=D=Y-X=m$\epsilon$
$D=k\sigma_y=k*\sqrt{Y}$, assuming that the distribution of Y follows that of Poisson (mean=standard deviation=Y)

$k=m\epsilon/\sqrt{Y}$ $m=Y/(2+\epsilon)$ $k=\sqrt{Y}*\epsilon/(2+\epsilon)$

If ⅓ of the panel is used (i.e., 1 positive compartment in every 3 compartments)
N=number of compartments $Y*=N/3$ $Y=\log(1-Y*/3)/\log(1-1/N)=\log(\frac{2}{3})/\log(1-1/N)$ k varies with N as shown in the graph.

The confidence interval k corresponds to the standard deviation, where a higher standard deviation indicates a greater difference between the normal and the Down's DNA. Even at the lowest concentration used (30%) and with only 10 panels analyzed, statistical analysis showed the feasibility of the present method.

FIGS. 2 and 3 show results from 100% Downs samples, for easy of visual analysis. In each panel, the number of white spots indicates the positive wells for the markers tested. Chromosome 21 can be seen to have more spots by simple visual observation, distinguishing the trisomic from the normal chromosome. In a 30% mixture (representing an enriched maternal blood sample), the results were analyzed statistically.

Table 1 below shows the results for each panel (numbered as in FIGS. 2 and 3) in a single experiment using 30% Down's DNA.

TABLE 1

| Panel | Sample | FAM | HEX | Ratio |
|---|---|---|---|---|
| 1 | Normal | 221 | 213 | 1.04 |
| 2 | Normal | 254 | 264 | 0.96 |
| 3 | Normal | 271 | 252 | 1.08 |
| 4 | Normal | 246 | 257 | 0.96 |
| 5 | Normal | 241 | 238 | 1.01 |
| 8 | 30% Downs | 270 | 222 | 1.22 |
| 9 | 30% Downs | 219 | 194 | 1.13 |
| 10 | 30% Downs | 249 | 234 | 1.06 |
| 11 | 30% Downs | 230 | 223 | 1.03 |
| 12 | 30% Downs | 216 | 189 | 1.14 |

The "FAM" column shows the compartments (wells) positive for chromosome 21, and the "HEX" column shows the compartments positive for chromosome 12. The significance of the higher ratios in the Downs cases is shown in FIG. 4, and was also analyzed in a Student's T-test, with a value of 0.036599344.

The above analysis shows that the statistical reliability of the present method can be dramatically improved simply by increasing the number of wells tested. Since about 240 genome equivalents is required per panel, and about 4,700 genome equivalents are found in a 20 ml sample, it is possible, given the present description, to simply run additional analyses to increase statistical significance.

CONCLUSION

The present examples, methods, procedures, specific compounds and molecules are meant to exemplify and illustrate the invention and should in no way be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but would be understood by workers in the field. Such patents or publications are hereby incorporated by reference to the same extent as if each was specifically and individually incorporated by reference and for the purpose of describing and enabling the method or material referred to. The exemplary protocols given are for the convenience of the reader and are not to be construed as necessary to one of ordinary skill in the art, given the teachings of the present specification regarding the various methods and materials to be used.

What is claimed is:

1. A method for identifying an abnormal fetal chromosome copy number by measuring target sequences in a mixture of maternal and fetal DNA, comprising the steps of:
   a) obtaining a maternal blood sample comprising a mixture of fragments of maternal and fetal DNA;
   b) distributing the mixture of maternal and fetal DNA into reaction samples containing on average one target sequence per reaction sample;
   c) in each reaction sample, identifying target sequences that are specific to a human chromosome suspected of being of an abnormal fetal copy number and target sequences on one or more human chromosomes that are presumably present in a normal copy number, wherein the identifying comprises (1) sequencing target chromosomal sequences on a chromosome suspected of being of an abnormal fetal copy number and target chromosomal sequences on one or more chromosomes of presumably normal copy number; (2) amplifying target chromosomal sequences on a chromosome suspected of being of an abnormal fetal copy number and target chromosomal sequences on one or more chromosomes of presumably normal copy number by polymerase chain reaction (PCR); or (3) hybridizing target chromosomal sequences on a chromosome suspected of being of an abnormal fetal copy number with a sequence-specific probe and hybridizing target chromosomal sequences on one or more chromosomes of presumably normal copy number with a sequence-specific probe;
   d) digitally counting the number of target sequences identified as belonging to a specific chromosome suspected of being of abnormal fetal copy number and the number of target sequences on one or more chromosomes of presumably normal copy number in the reaction samples; and
   e) detecting a significantly different number of target sequences on chromosomes suspected of being of abnormal fetal copy number compared to the number of target sequences on the one or more chromosomes of presumably normal copy number in the reaction samples, thereby identifying an abnormal fetal chromosome copy number.

2. The method of claim 1 wherein the target sequences on the human chromosome suspected of being of abnormal fetal copy number comprise chromosome 21 sequences and wherein the abnormal number of chromosomes is trisomy for chromosome 21.

3. The method of claim 1 wherein the reaction samples are in reaction samples selected from the group consisting of:

wells in a microtiter plate, aqueous phases in an emulsion, an area on an array surface, and reaction chambers in a microfluidic device.

4. The method of claim 1 wherein the identifying in step (c) comprises amplifying target chromosomal sequences suspected of being present in an abnormal fetal copy number and target chromosomal sequences of presumably normal fetal copy number by PCR.

5. The method of claim 1 wherein the mixture of maternal and fetal DNA is distributed into at least about 10,000 reaction samples.

6. The method of claim 1 wherein the target sequences on the human chromosome suspected of being of abnormal fetal copy number comprise chromosome 21 sequences and wherein the target sequences on the one or more chromosomes of presumably normal fetal copy number are specific for another human chromosome.

7. The method of claim 1 further comprising, prior to step (b), the step of enriching the mixture for fetal DNA by size separation, whereby a preparation comprising only DNA fragments less than about 300 bp is used for distributing in step (b).

8. The method of claim 1 in which the identifying in step (c) comprises sequencing target chromosomal sequences suspected of being present in an abnormal fetal copy number and target chromosomal sequences of presumably normal fetal copy number.

9. The method of claim 4, wherein FOR is performed by contacting DNA in the reaction samples with a plurality of FOR primers.

* * * * *

UNITED STATES PATENT AND TRADEMARK OFFICE
CERTIFICATE OF CORRECTION

PATENT NO. : 9,777,329 B2  
APPLICATION NO. : 12/689548  
DATED : October 3, 2017  
INVENTOR(S) : Stephen Quake et al.

Page 1 of 1

It is certified that error appears in the above-identified patent and that said Letters Patent is hereby corrected as shown below:

In the Claims

Column 35, Line 28, Claim 9, "FOR" should be -- PCR --;

Column 35, Line 30, Claim 9, "FOR" should be -- PCR --.

Signed and Sealed this
Twenty-fourth Day of April, 2018

Andrei Iancu
*Director of the United States Patent and Trademark Office*

SEQUENCE LISTING

<160> NUMBER OF SEQ ID NOS: 16

<210> SEQ ID NO 1
<211> LENGTH: 24
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 1
gggagctggt acagaaatga cttc                                            24

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
agccatcctt cccgggccta gg                                              22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccccacacac atgcacttac c                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctactccca gggctttgat t                                               21

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
aaagagctag gaaggacagg caacttggc                                       29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
aggttgtgaa aacagcagca atgcaatgt                                       29

<210> SEQ ID NO 7
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 7
ccacaggaag ccgcctagt                                                19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgagggaaga aaggaaacgc t                                             21

<210> SEQ ID NO 9
<211> LENGTH: 84
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccacaggaag ccgcctagtg cagagaggtt gtgaaaacag cagcaatgca atgtggaaat   60
tgtagcgttt cctttcttcc ctca                                          84

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgctcattg cgctgacaa                                                19

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggagctggt acagaaatga cttc                                          24

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttgctcattg cgctgacaa                                                19

<210> SEQ ID NO 13
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 13
agccatcctt cccgggccta gg                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccccacacac atggcactta cc                                              22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cctagtccca gggctttgat t                                               21

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaagagctag gaaggacagg caacttggc                                       29
```